(12) United States Patent
Ino et al.

(10) Patent No.: US 10,503,109 B2
(45) Date of Patent: Dec. 10, 2019

(54) OPTICAL SENSOR HAVING AN IRRADIATING LIGHT SEPARATION COMPONENT AND IMAGE FORMING APPARATUS THEREOF

(71) Applicant: CANON KABUSHIKI KAISHA, Tokyo (JP)

(72) Inventors: Kazushi Ino, Suntou-gun (JP); Chihiro Nagura, Yokohama (JP); Takuya Mukaibara, Susono (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/945,261

(22) Filed: Apr. 4, 2018

(65) Prior Publication Data
US 2018/0292776 A1    Oct. 11, 2018

(30) Foreign Application Priority Data

Apr. 10, 2017 (JP) .................................. 2017-077734

(51) Int. Cl.
*G03G 15/00* (2006.01)
*G01N 21/55* (2014.01)

(52) U.S. Cl.
CPC ......... *G03G 15/5058* (2013.01); *G01N 21/55* (2013.01); *G01N 2201/068* (2013.01); *G01N 2201/0638* (2013.01); *G01N 2201/0639* (2013.01); *G03G 2215/00042* (2013.01)

(58) Field of Classification Search
CPC ............................................... G03G 15/5058
USPC ......................................................... 399/74
See application file for complete search history.

(56) References Cited

U.S. PATENT DOCUMENTS

| 6,229,721 B1 | 5/2001 | Mano et al. |
| 9,075,368 B2 | 7/2015 | Mukaibara |
| 9,766,096 B2 | 9/2017 | Nagura |
| 2010/0054774 A1* | 3/2010 | Yamasaki .......... G03G 15/0131 399/49 |

(Continued)

FOREIGN PATENT DOCUMENTS

| JP | H10-221902 A | 8/1998 |
| JP | 2006-208266 A | 8/2006 |

(Continued)

OTHER PUBLICATIONS

Office Action in Japanese Patent Application No. 2017-077734, dated Jun. 4, 2018.

(Continued)

*Primary Examiner* — Walter L Lindsay, Jr.
*Assistant Examiner* — Philipmarcus T Fadul
(74) *Attorney, Agent, or Firm* — Venable LLP

(57) ABSTRACT

A toner detection unit (optical sensor) includes a first light receiving element configured to receive specular reflection light of first irradiating light, and a second light receiving element configured to receive diffused reflection light of second irradiating light, and a separation component configured to separate irradiating light emitted from an LED into the first and second irradiating light. A housing forms a first opening through which the first irradiating light and the second irradiating light pass and the diffused reflection light to be received by the second light receiving element passes, and a second opening through which the specular reflection light to be received by the first light receiving element passes.

22 Claims, 17 Drawing Sheets

(56) References Cited

U.S. PATENT DOCUMENTS

| | | | |
|---|---|---|---|
| 2013/0243466 A1* | 9/2013 | Taishi | G03G 15/5025 |
| | | | 399/74 |
| 2013/0272740 A1 | 10/2013 | Nakagawa et al. | |
| 2015/0211992 A1* | 7/2015 | Ishizumi | G01N 21/55 |
| | | | 399/49 |
| 2015/0247724 A1 | 9/2015 | Yuki et al. | |
| 2017/0131657 A1 | 5/2017 | Monden et al. | |
| 2017/0131670 A1 | 5/2017 | Ino et al. | |

FOREIGN PATENT DOCUMENTS

| | | |
|---|---|---|
| JP | 2008-261864 A | 10/2008 |
| JP | 2010-230878 A | 10/2010 |
| JP | 2012-198188 A | 10/2012 |
| JP | 2013-113750 A | 6/2013 |
| JP | 2013-191835 A | 9/2013 |
| JP | 2013-195066 A | 9/2013 |
| JP | 2014-026225 A | 2/2014 |
| JP | 2015-161633 A | 9/2015 |
| JP | 2017-090597 A | 5/2017 |
| JP | 2017-090599 A | 5/2017 |

OTHER PUBLICATIONS

Office Action in Japanese Patent Application No. 2017-077734, dated Dec. 7, 2018.

* cited by examiner

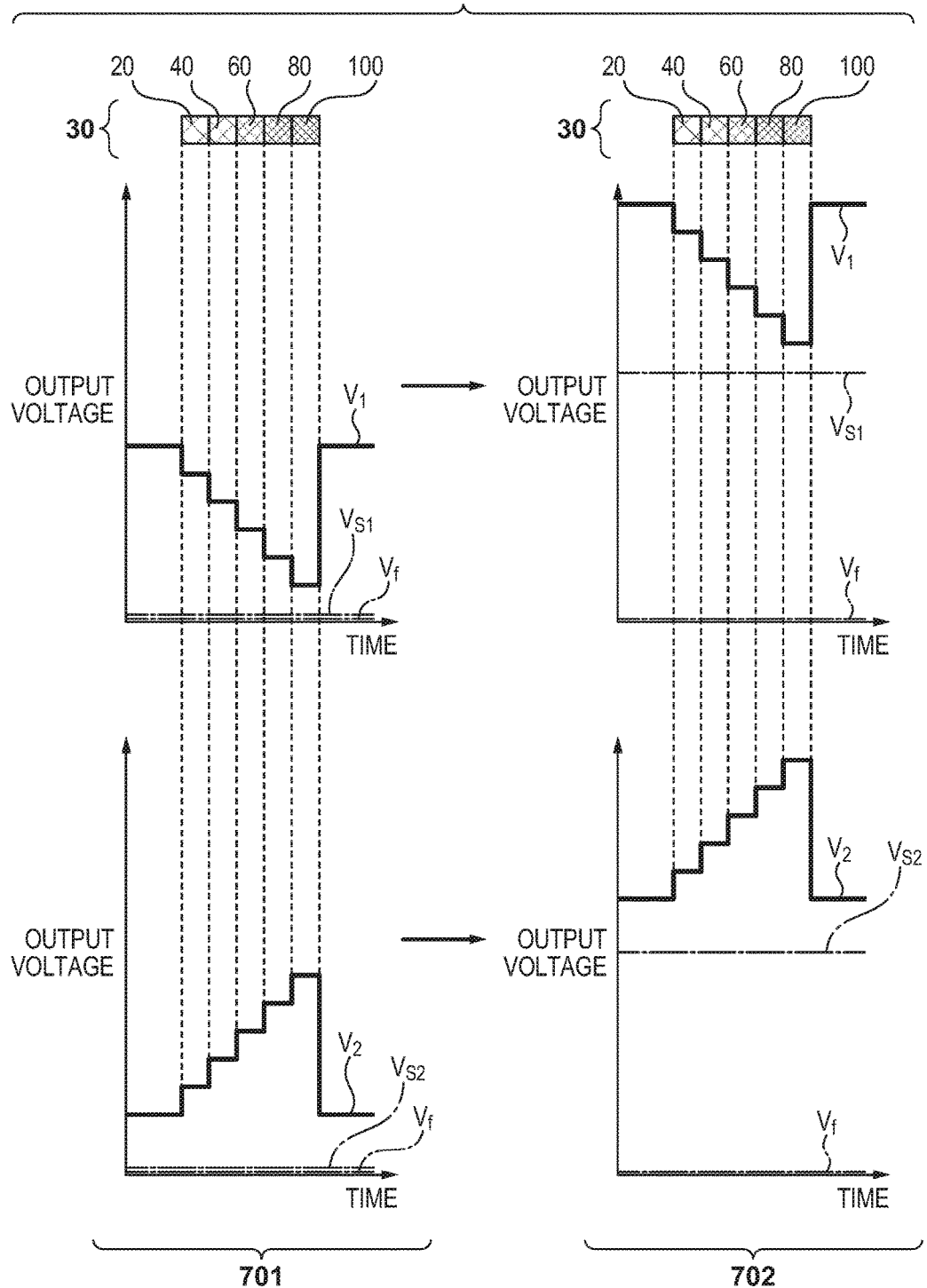

OPTICAL SENSOR HAVING AN IRRADIATING LIGHT SEPARATION COMPONENT AND IMAGE FORMING APPARATUS THEREOF

BACKGROUND OF THE INVENTION

Field of the Invention

The present invention relates to an optical sensor for detecting a detection target by receiving, by a plurality of light receiving elements, a specular reflection light and a diffused reflection light of light emitted from a light emitting element, and an image forming apparatus comprising the optical sensor.

Description of the Related Art

In recent years, in electrophotographic image forming apparatuses, a tandem type which is a configuration in which a photosensitive member is arranged for each color to accelerate printing speed has become mainstream. In a tandem type image forming apparatus, a color misregistration amount is determined by forming a detection image (a toner image) which is a test pattern for detecting a color misregistration amount on an intermediate transfer belt, for example, and then irradiating light onto the detection image and detecting light reflected therefrom by an optical sensor. Also, a determination of a density of a toner (a density of an image) using such an optical sensor has been performed. In Japanese Patent Laid-Open No. H10-221902, a technique is disclosed in which a diffused reflection light and a specular reflection light of light irradiated on a toner image are respectively received by individual light receiving units (sensors), and based on the received light amounts, the density of toner is detected. By virtue of such a technique, it is possible to improve precision of detection of toner by an optical sensor even if toner of a plurality of colors used in the image forming apparatus has reflection characteristics that differ with respect to the light used by the optical sensor.

In an optical sensor of the foregoing type, generally, in addition to providing an aperture for limiting (narrowing) light that the light emitting element emits, that kind of aperture is also provided for the light receiving elements that respectively receive specular reflection light and diffused reflection light in order to separate the specular reflection light and the diffused reflection light. Surface-mounted type optical sensors in which an optical element is mounted directly on a surface of a circuit board are disclosed as such kind of optical sensors in Japanese Patent Laid-Open No. 2006-208266 and in Japanese Patent Laid-Open No. 2013-191835.

In Japanese Patent Laid-Open No. 2006-208266, an optical unit holder is attached to a circuit board on which a light emitting element and two light receiving elements are directly mounted, and three polarization filters respectively corresponding to the light emitting element and the two light receiving elements are arranged on an outside surface of the optical unit holder. However, when a plurality of polarization filters are used in this way, it leads to an increase in apparatus cost, and a reduction in productivity. Meanwhile, in Japanese Patent Laid-Open No. 2013-191835, a housing having an opening (a light guiding path) that functions as an aperture corresponding to each optical element (the light emitting element and the two light receiving elements) is configured such that light shielding walls that configure the openings are inserted in a slit hole arranged in a circuit board. This improves a light-shielding property in an optical sensor configured by mounting each optical element on a surface of the circuit board.

However, in the optical sensor described in Japanese Patent Laid-Open No. 2013-191835, it is necessary to arrange the light emitting element and the two light receiving elements at a certain distance from each other in order to realize the housing that improves the light-shielding property. Even if it is possible to improve the light-shielding property by virtue of this kind of optical sensor configuration, the size of the optical sensor is larger in a direction in which the light emitting element and the two light receiving elements are arranged. Accordingly, it would be desirable to realize further miniaturization in the optical sensor.

SUMMARY OF THE INVENTION

The present invention was conceived in view of the above described issues. The present invention provides a technique that enables the miniaturization of an optical sensor for detecting a detection target by receiving, by different light receiving elements, a specular reflection light and a diffused reflection light of light emitted from a light emitting element.

According to one aspect of the present invention, there is provided an optical sensor comprising: a light emitting element configured to emit irradiating light with which an irradiated member is irradiated; a separation component configured to separate the irradiating light into first irradiating light and second irradiating light; a first light receiving element configured to receive specular reflection light specularly reflected by the irradiated member when irradiation with the first irradiating light is performed; a second light receiving element configured to receive diffused reflection light diffusely reflected by the irradiated member when irradiation with the second irradiating light is performed; and a housing configured to form a first opening through which the first irradiating light and the second irradiating light pass and the diffused reflection light to be received by the second light receiving element passes, and a second opening through which the specular reflection light to be received by the first light receiving element passes.

According to another aspect of the present invention, there is provided an image forming apparatus comprising: an image carrier; an image forming unit configured to form an image on the image carrier; an optical sensor provided at a position opposing a surface of the image carrier and configured to irradiate the image carrier as an irradiated member with light from a light emitting element; and a control unit configured to control an image forming condition of the image forming unit based on a signal from the optical sensor, wherein the optical sensor comprises: the light emitting element configured to emit irradiating light with which the irradiated member is irradiated; a separation component configured to separate the irradiating light into first irradiating light and second irradiating light; a first light receiving element configured to receive specular reflection light specularly reflected by the irradiated member when irradiation with the first irradiating light is performed; a second light receiving element configured to receive diffused reflection light diffusely reflected by the irradiated member when irradiation with the second irradiating light is performed; and a housing configured to form a first opening through which the first irradiating light and the second irradiating light pass and the diffused reflection light to be received by the second light receiving element passes, and a second opening through which the specular reflection light to be received by the first light receiving element passes.

By virtue of the present invention, it becomes possible to miniaturize an optical sensor for detecting a detection target by receiving, by different light receiving elements, a specular reflection light and a diffused reflection light of light emitted from a light emitting element.

Further features of the present invention will become apparent from the following description of exemplary embodiments (with reference to the attached drawings).

BRIEF DESCRIPTION OF THE DRAWINGS

FIG. 3 is a perspective view illustrating an arrangement example of a toner detection unit 31 in relation to an intermediate transfer belt 12a.

FIG. 7 illustrates examples of the output characteristics of light receiving elements 34 and 35 of a toner detection unit 131 according to a comparative example.

DESCRIPTION OF THE EMBODIMENTS

Hereinafter, embodiments of the present invention will be described in detail with reference to the accompanying drawings. It should be noted that the following embodiments are not intended to limit the scope of the appended claims, and that not all the combinations of features described in the embodiments are necessarily essential to the solving means of the present invention.

First Embodiment

<Overview of Image Forming Apparatus>

Figure 1:
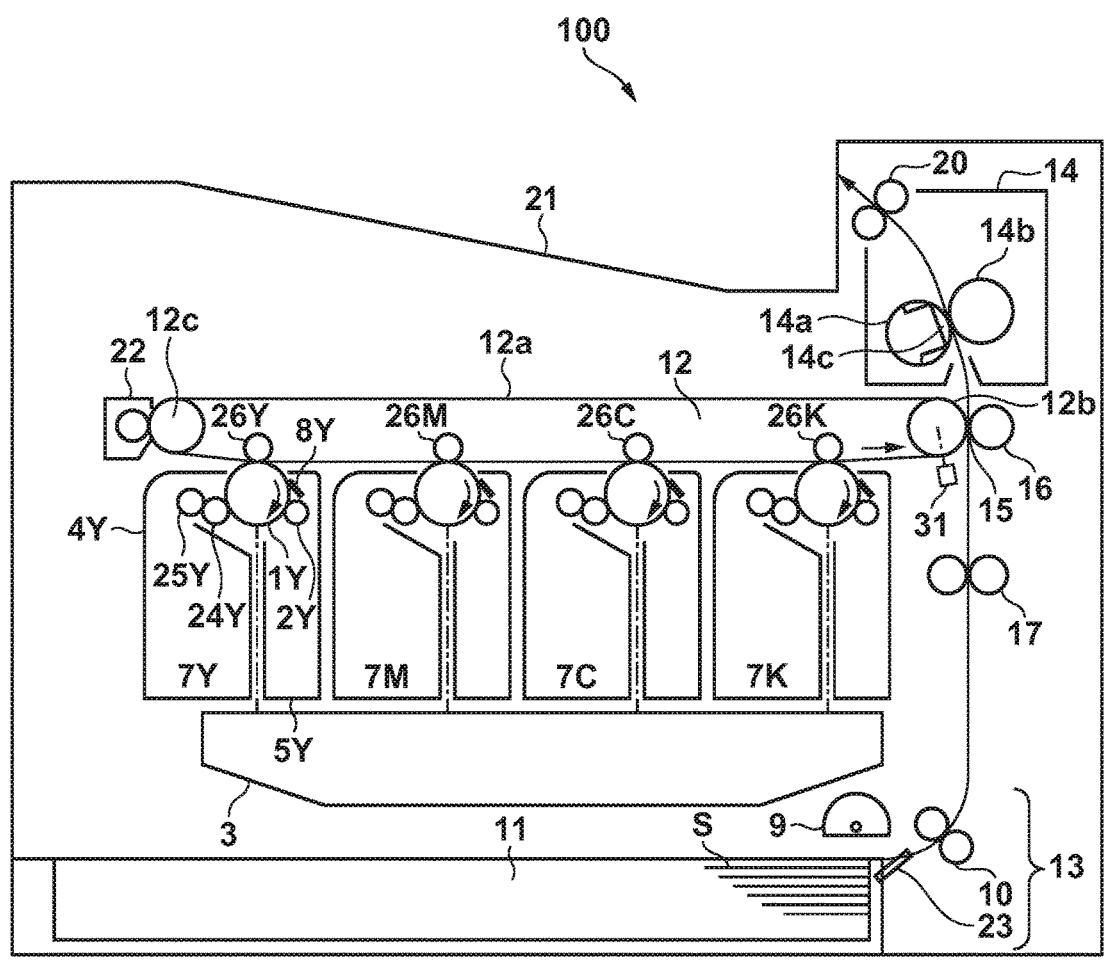
FIG. 1 is a cross-section view for illustrating an example of a hardware configuration of an image forming apparatus.

FIG. 1 is a cross-section view for illustrating an example of a hardware configuration of an image forming apparatus 100 according to a first embodiment. The image forming apparatus 100 in the present embodiment is a color laser printer for forming a multicolor image using developing material (toner) of yellow (Y), magenta (M), cyan (C), and black (K). The image forming apparatus 100 may also be any of the following: for example a print apparatus, a printer, a copying machine, a multi function peripheral (MFP), or a facsimile apparatus. Note that Y, M, C, or K on the end of reference numerals indicates that the color of the developing material (toner) of the corresponding component is yellow, magenta, cyan, or black. In the following explanation, reference numerals are used omitting the Y, M, C, or K on the end in a case where it is not necessary to distinguish the color.

The image forming apparatus 100 is equipped with 4 process cartridges 7 (process cartridges 7Y, 7M, 7C, and 7K) corresponding to image forming stations for forming images of Y, M, C, and K respectively. In FIG. 1, reference numerals are given only for components of the process cartridge 7Y corresponding to Y, but the same configuration is employed for the four process cartridges 7Y, 7M, 7C, and 7K. However, the four process cartridges 7Y, 7M, 7C, and 7K are different in that they form images by respectively different colored (Y, M, C, and K) toner.

In a periphery of a photosensitive drum 1, a charging roller 2, an exposure unit 3, a developing unit 4, a primary transfer roller 26, and a cleaning blade 8 are arranged sequentially in a rotation direction. In the present embodiment, the photosensitive drum 1, the charging roller 2, the developing unit 4 and the cleaning blade 8 are integrated into the process cartridge 7 which can be attached/removed to/from the image forming apparatus 100. The exposure unit 3 is arranged on a lower side in a vertical direction of the process cartridge 7.

The process cartridge 7 is configured by the developing unit 4 and a cleaner unit 5. The developing unit 4 includes a developing roller 24, a developing material coating roller 25, and a toner container. Toner of the corresponding color is contained in a toner container. The developing roller 24 is rotated by a drive motor (not shown), a developing bias voltage is applied from a high voltage power supply 44 (FIG. 2), and development of an electrostatic latent image is performed using toner contained in the toner container. The cleaner unit 5 includes the photosensitive drum 1, the charging roller 2, the cleaning blade 8, and a waste toner container.

The photosensitive drum 1 is configured by an organic photo conductor layer (OPC) coated on an outer surface of an aluminum cylinder. The photosensitive drum 1 is supported to be rotatable by flanges on both ends, and is rotated in a direction of an arrow illustrated in FIG. 1 by a driving force being transferred from a drive motor (not shown) to one end. The charging roller 2 uniformly charges the surface of the photosensitive drum 1 to a predetermined electric potential. The exposure unit 3 irradiates a laser beam on the photosensitive drum 1 to expose the photosensitive drum 1 based on image information (image signal), thereby forming an electrostatic latent image on the photosensitive drum 1. The developing unit 4 forms a toner image on the photosensitive drum 1 by causing toner to attach in an electrostatic latent image on the photosensitive drum 1 and then developing the electrostatic latent image.

Figure 2:
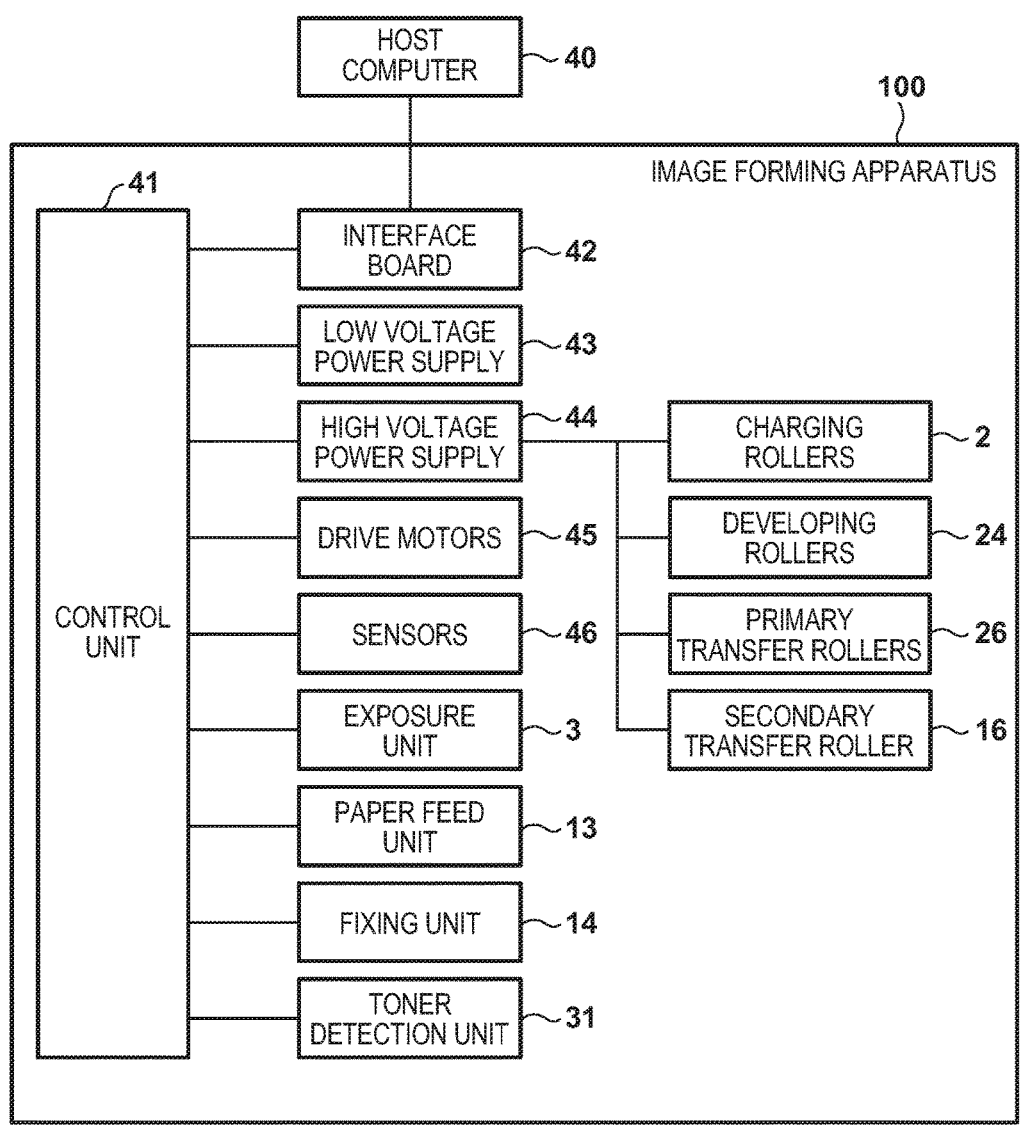
FIG. 2 is a block diagram illustrating an example configuration of a control system of the image forming apparatus.

An intermediate transfer belt 12a, a driving roller 12b, and a tension roller 12c configure an intermediate transfer unit 12. The intermediate transfer belt 12a is stretched between the driving roller 12b and the tension roller 12c, and moves (rotates) in a direction of an arrow illustrated in FIG. 1 by a rotation of the driving roller 12b. In the present embodiment, the intermediate transfer belt 12a is an example of an image carrier which is rotated. At a position inside of the intermediate transfer belt 12a and facing the photosensitive drum 1, the primary transfer roller 26 is arranged. The primary transfer roller 26 transfers a toner image on the photosensitive drum 1 onto the intermediate transfer belt 12a (an intermediate transfer member) by a transfer bias voltage applied from the high voltage power supply 44 (FIG. 2). Toner images of the four colors respectively formed on the photosensitive drums 1Y, 1M, 1C, and 1K are transferred (primary transfer) on the intermediate transfer belt 12a sequentially so as to overlap each other. Thus, a multicolor toner image composed of Y, M, C, and K is formed on the intermediate transfer belt 12a. The multicolor toner image formed on the intermediate transfer belt 12a is conveyed to a secondary transfer nip portion 15 between the intermediate transfer belt 12a and a secondary transfer roller 16 in accordance with a rotation of the intermediate transfer belt 12a.

A paper feed unit 13 includes a paper feed roller 9, a conveyance roller pair 10, a paper feed cassette 11, and a separation pad 23. A sheet S set by a user is contained in the feed cassette 11. The sheet S may be called recording paper, recording material, recording medium, paper, transfer material, transfer paper, or the like. The paper feed roller 9 feeds the sheet S from the feed cassette 11 to a conveyance path. Note that the sheet S contained in the feed cassette 11 is fed to the conveyance path by the separation pad 23 one sheet at a time. The conveyance roller pair 10 conveys the sheet S fed on the conveyance path toward a registration roller pair 17. When the sheet S is conveyed to the registration roller pair 17, in synchronization with a timing at which the toner image on the intermediate transfer belt 12a reaches the secondary transfer nip portion 15, the sheet S is conveyed to the secondary transfer nip portion 15 by the registration roller pair 17. Thus, the toner image on the intermediate transfer belt 12a is transferred (secondary transfer) onto the sheet S in the secondary transfer nip portion 15.

The sheet S onto which the toner image is transferred is conveyed to a fixing unit 14. The fixing unit 14 includes a fixing belt 14a, a pressure roller 14b, and a belt guide component 14c, and the fixing belt 14a is guided to a belt guide component 14c to which a heat generation device such as a heater is bonded. The fixing nip portion is formed between the fixing belt 14a and the pressure roller 14b. The fixing unit 14 fixes the toner image on the sheet S by applying heat and pressure to the toner image formed on the sheet S in the fixing nip portion. After the fixing process by the fixing unit 14, the sheet S is discharged to a sheet discharge tray 21 by a discharge roller pair 20.

Toner remaining on the photosensitive drum 1 after the primary transfer of the toner image to the intermediate transfer belt 12a is removed from the photosensitive drum 1 by the cleaning blade 8 and collected into a waste toner container in the cleaner unit 5. Also, toner remaining on the intermediate transfer belt 12a after the secondary transfer of the toner image to the sheet S is removed from the intermediate transfer belt 12a by a cleaner unit 22, and then collected in the waste toner container (not shown graphically) via a waste toner conveyance path.

A toner detection unit 31 (optical sensor) is arranged at a position facing the driving roller 12b in the image forming apparatus 100. The toner detection unit 31 can optically detect toner on the intermediate transfer belt 12a as will be described later. The image forming apparatus 100 according to the present embodiment forms a test pattern constituted by a toner image on the intermediate transfer belt 12a, and detects the test pattern formed on the intermediate transfer belt 12a by the toner detection unit 31. Additionally, the image forming apparatus 100 performs a later described calibration based on the result of the detection of the test pattern by the toner detection unit 31.

<Control Configuration of Image Forming Apparatus>

FIG. 2 is a block diagram for illustrating an example configuration of a control system of the image forming apparatus 100 according to the present embodiment. Note that in FIG. 2, only devices necessary for the explanation of the present embodiment are illustrated. The image forming apparatus 100 is equipped with a control unit 41, which incorporates a microcomputer, as an engine control unit. The image forming apparatus 100 further comprises, as devices that are connected to enable communication with the control unit 41, an interface (I/F) board 42, a low voltage power supply 43, the high voltage power supply 44, various drive motors 45, various sensors 46, the exposure unit 3, the paper feed unit 13, the fixing unit 14, and the toner detection unit 31.

The I/F board 42 is capable of communicating with a host computer 40, which is external to the image forming apparatus 100, via a network such as a LAN. The low voltage power supply 43 supplies voltage to the control unit 41 for the control unit 41 to operate. The high voltage power supply 44 supplies, in accordance with control by the control unit 41, a bias voltage to the charging rollers 2, the developing rollers 24, the primary transfer rollers 26, and the secondary transfer roller 16 at a time of image formation execution. Among the various drive motors 45 are included a drive motor for rotating the photosensitive drums 1, a drive motor for rotating the developing rollers 24, and the like. Among the various sensors 46 are included sensors other than the toner detection unit 31 such as a sensor for detecting a sheet S conveyed along the conveyance path. The control unit 41, by controlling the various devices illustrated in FIG. 2 based on various signals such as an output signal of the toner detection unit 31, output signals of the various sensors 46, or the like, executes various control such as sequence control for calibration of the image forming apparatus 100 and image formation.

<Calibration of Image Forming Apparatus>

Figure 3:
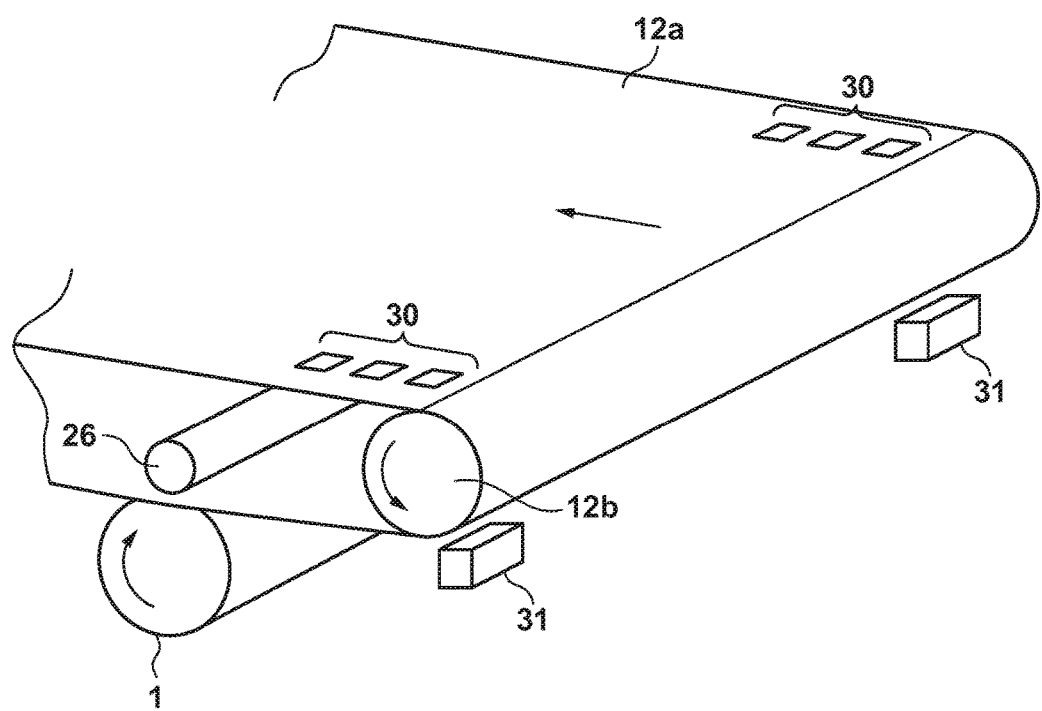

Next, with reference to FIG. 3, a calibration of the image forming apparatus 100 (automatic correction control) will be described. FIG. 3 is a perspective view illustrating an arrangement example of the toner detection unit 31 in relation to the intermediate transfer belt 12a, and illustrates an example of a state of the intermediate transfer belt 12a at a time of calibration execution. Broadly divided, the calibration of the image forming apparatus 100 includes two kinds of control: "color misregistration correction control" and "image density control". These two kinds of control are both performed by forming a test pattern 30 on the intermediate transfer belt 12a while the image forming apparatus 100 is not performing image formation to a sheet S, and optically detecting the formed test pattern 30 by the toner detection unit 31.

If the test pattern 30 is detected by the toner detection unit 31 on a flat portion of the intermediate transfer belt 12a, it is difficult to obtain satisfactory sensor output due to vibration and the like at the time of belt movement. Accordingly, the toner detection unit 31 is arranged at a position facing the driving roller 12b via the intermediate transfer belt 12a as illustrated in FIG. 3 rather than at a position facing the flat portion of the intermediate transfer belt 12a. The test pattern 30 formed on the surface (outer surface) of the intermediate transfer belt 12a is detected by the toner detection unit 31 at a position facing the driving roller 12b when it passes the position of the driving roller 12b. Also, so that it is possible to detect the test pattern 30 at least two positions in a direction orthogonal to the movement direction of the surface of the intermediate transfer belt 12a, at least two toner detection unit 31 are arranged in such an orthogonal direction. Below, both the color misregistration correction control and the image density control will be described more specifically.

(Color Misregistration Correction Control)

The color misregistration correction control corresponds to color misregistration correction control in which an amount of relative positional misalignment (color misregistration) between the image forming stations for toner images formed by the respective image forming stations is measured, and correction of the color misregistration is performed based on the measurement results. The control unit 41 performs a color misregistration correction control by adjusting the timing at which each line is started to be written in addition to controlling the exposure units 3 so that a scanning speed and an amount of exposure light of laser beam on the photosensitive drums 1 becomes a predetermined speed and a predetermined amount of light.

For example, if the exposure unit 3 is of a polygon mirror type, the control unit 41, upon image formation, generates an image top signal by counting write start reference pulses from the exposure unit 3, and outputting the generated image top signal to the I/F board 42. The I/F board 42 outputs, in synchronization with the image top signal, exposure data one line at a time (one surface of a polygon mirror) to the exposure unit 3 via the control unit 41. By causing the output timing of the image top signal from the control unit 41 to change by an amount of time corresponding to a few dots for each image forming station, it is possible to cause the timing at which each line is started to be written to change by a few dots. With this, it is possible to adjust an image write start position in the main scanning direction of the photosensitive drum 1. Also, by causing the write timing to change in units of lines, it is possible to cause the whole image to shift in a conveyance direction (a sub scanning direction) of the toner image on the photosensitive drum 1. With this, it is possible to adjust an image write start position in the sub scanning direction of the photosensitive drum 1. Also, by controlling a difference in a rotational phase of the polygon mirror of the exposure unit 3 between the image forming stations, it is possible to perform alignment of the images of the respective colors in the sub scanning direction at a resolution of one line or less. Furthermore, it is possible to perform correction of a main-scanning magnification by causing the clock frequency to be used as the reference of ON/OFF in the exposure data to change.

In this way, correction of a color misregistration between image forming stations in the color misregistration correction control can be realized by adjusting a reference clock and an image formation timing. To realize the color misregistration correction control, it is necessary to measure the relative color misregistration amounts between the image forming stations as described above. In the color misregistration correction control, a test pattern for a color misregistration amount measurement of at least two columns on the intermediate transfer belt 12a is formed for each color, and positions (a time of passage of a position facing the optical sensor) of the test pattern are detected by at least two optical sensors (the toner detection unit 31). The control unit 41, based on the results of this detection, calculates a relative color misregistration amount in the main scanning direction and the sub scanning direction between the image forming stations, a magnification factor of the main scanning direction, and a relative tilt. Furthermore, the control unit 41 performs a color misregistration correction as described above so that the color misregistration amount between the image forming stations becomes small.

(Image Density Control)

Image density control is control for correcting an image forming condition so that a density characteristic of an image formed by the image forming apparatus 100 becomes a desired density characteristic. In the image forming apparatus 100, due to temperature and humidity conditions and the levels of usage of the image forming stations of the respective colors, a density characteristic of formed images (toner images) changes. Image density control is performed to correct these changes. Specifically, the test pattern 30 is formed on the intermediate transfer belt 12a, and based on the result of detection of the test pattern 30 by the toner detection unit 31, an image forming condition is adjusted so as to obtain a desired density characteristic. Note that the test pattern 30 may be generated by the control unit 41, or may be generated by an external apparatus (for example, the host computer 40).

The control unit 41 (CPU) calculates (detects a density of a toner image) a value corresponding to a density of the toner image which is the test pattern 30 from a received light amount signal after A/D (analog/digital) conversion which is outputted from the toner detection unit 31. Furthermore, the control unit 41, based on the result of the detection of the density of the toner image, sets the image forming condition to be used when performing image formation. The image forming condition that is set is a charge bias voltage, a developing bias voltage, an amount of exposure light (the laser power of the exposure unit 3), or the like, for example. By repeating such settings, it is possible to optimize an image forming condition related to an image density characteristic. Note that the control unit 41 stores in a memory within the control unit 41 the image forming condition that has been set, so as to be able to use it at a time of image formation and at a time of the next image density control.

By performing such image density control, it is possible to adjust the maximum density of each color to a desired value, and it is possible to prevent the occurrence of an image defect called "fogging" in which unwanted toner adheres to a white background portion of an image. Also, by performing the image density control, it is possible to keep fixed the color balance of the respective colors, and to prevent an image defect and a fixing defect due to excessive application of toner.

<Configuration of Toner Detection Unit>

Figure 4:
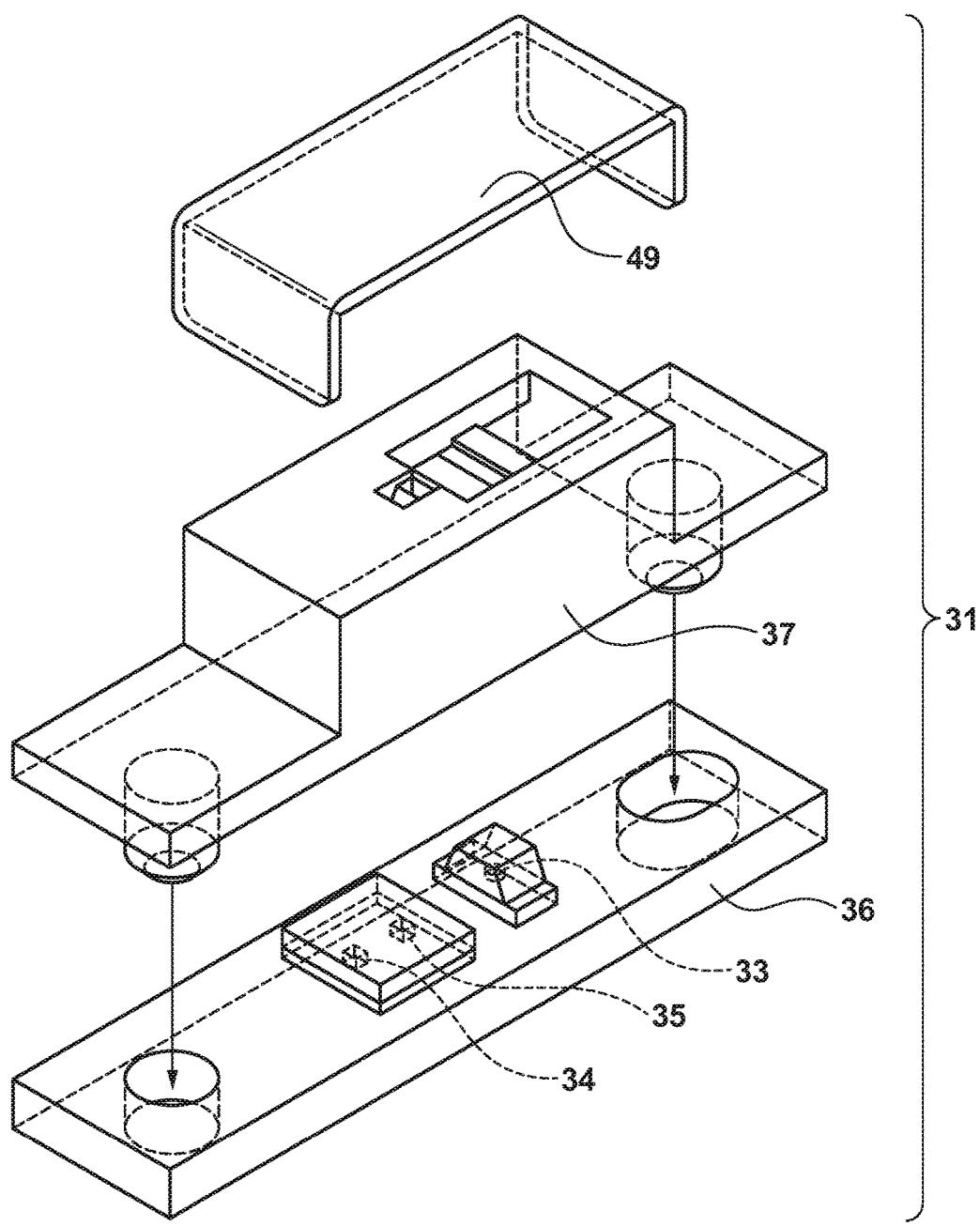
FIG. 4 is a perspective view illustrating an example configuration of the toner detection unit 31.
Figure 5A:
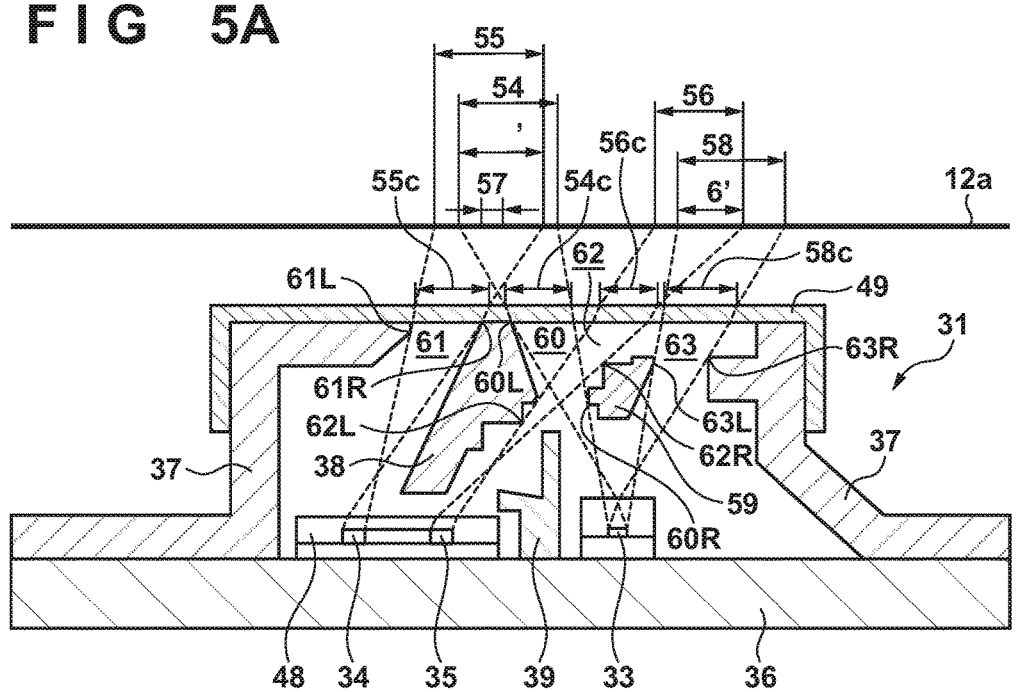
FIG. 5A and FIG. 5B are cross-sectional views illustrating an example configuration of the toner detection unit 31.
Figure 5B:
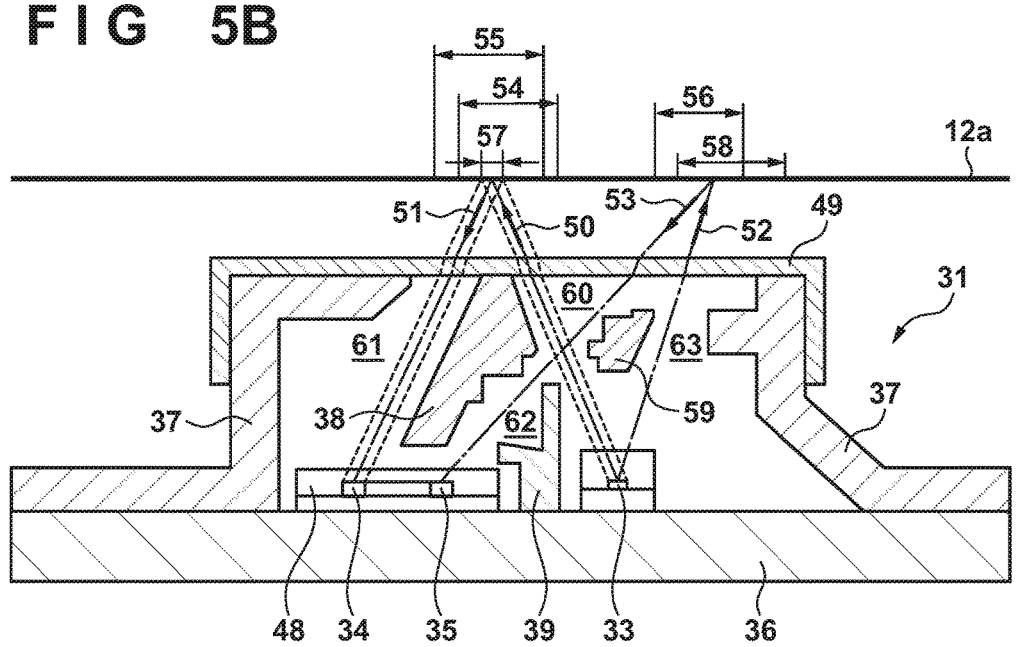

The configuration of the toner detection unit 31 for detecting the test pattern 30 will be described next. FIG. 4 is a perspective view illustrating an example configuration of the toner detection unit 31. FIGS. 5A and 5B are schematic cross-sectional views illustrating the example configuration of the toner detection unit 31. The toner detection unit 31 includes, as optical elements, an LED 33 (light emitting element) and two light receiving elements 34 and 35. As shown in FIG. 4, the toner detection unit 31 has a configuration in which a housing 37 is fixed to a circuit board 36 by inserting a projection portion of the housing 37 into a hole formed in the circuit board 36. The housing 37 is made of a material having a light shielding property, and covers the LED 33 and the two light receiving elements 34 and 35. The toner detection unit 31 also has a configuration in which a protection cover 49 (cover component) is mounted on the housing 37. The protection cover 49 is a component made of a material having a transmissive property (light transmissive property), and covers an opening formed by the housing 37 for dustproof of the LED 33 and the two light receiving elements 34 and 35. Note that FIGS. 5A and 5B show a state in which the housing 37 is fixed to the circuit board 36 and the protection cover 49 is mounted on the housing 37.

The LED 33 is used to irradiate, with light, the intermediate transfer belt 12a as an irradiated member (that is, to irradiate, with light, the intermediate transfer belt 12a to which toner as a detection target (measurement object) adheres), and emits irradiating light with which the irradiated member is irradiated. The light receiving elements 34 and 35 are respectively used to receive the specular reflection light and diffused reflection light of the light with which the intermediate transfer belt 12a is irradiated by the LED 33. In the toner detection unit 31, the housing 37 is configured to guide, to the light receiving elements 34 and 35, the specular reflection light and diffused reflection light of the light with which the intermediate transfer belt 12a is irradiated by the LED 33.

As shown in FIGS. 4, 5A, and 5B, the LED 33 and the two light receiving elements 34 and 35 are directly mounted on the surface (mounting surface) of the same circuit board 36, and arranged in a line on the circuit board. The light receiving elements 34 and 35 are arranged to be adjacent to each other on the circuit board 36. In the present embodiment, the light receiving element 34 is arranged at a position farther from the LED 33 than the light receiving element 35, and the light receiving element 35 is arranged at a position closer to the LED 33 than the light receiving element 34. That is, the linear distance between the light receiving element 35 and the LED 33 is shorter than that between the light receiving element 34 and the LED 33.

The light receiving elements 34 and 35 according to the present embodiment are configured by an integrated circuit (IC) in which phototransistors (semiconductors) having sensitivities to the wavelengths of light emitted from the LED 33 are integrated and COB-mounted on a substrate. The phototransistors mounted on the substrate are covered by a resin material (clear mold 48) having a transmissive property. The substrate on which the light receiving elements 34 and 35 are mounted is arranged on the circuit board 36. The LED 33 (light emitting element) and the light receiving elements 34 and 35 according to the present embodiment use infrared light. However, a light emitting element and light receiving elements that use light of other wavelengths may be adopted in the toner detection unit 31 if the light is of a wavelength to which the light receiving elements are sensitive depending on the combination of the light emitting element and the light receiving elements. In addition, in place of phototransistors, photodiodes may be used as the light receiving elements 34 and 35.

As shown in FIG. 5A, the housing 37 of the toner detection unit 31 includes light shielding walls 38 and 39. Furthermore, a separation component 59 made of a material having a light shielding property is provided at a position opposing (immediately above) the LED 33 (that is, above, in a vertical direction in relation to a flat surface on which the LED 33 is arranged) in the housing 37. The separation component 59 may be formed integrally with the housing 37. In the housing 37, a plurality of openings are formed by the inner wall of the housing 37, the light shielding walls 38 and 39, and the separation component 59, and light guiding paths 60 to 63 are configured by the plurality of openings.

The light guiding paths 60 and 63 are light guiding paths for guiding, to the intermediate transfer belt 12a, the light (irradiating light) emitted from the LED 33. The light guiding paths 61 and 62 are light guiding paths for guiding, respectively to the light receiving elements 34 and 35, the reflection light of the light emitted from the LED 33. A material having a light shielding property can be used for walls forming the light guiding paths.

The light guiding paths 60 and 63 are separated by the separation component 59. The irradiating light emitted from the LED 33 is separated, by the separation component 59, into light (first irradiating light) passing through the light guiding path 60 and light (second irradiating light) passing through the light guiding path 63, and guided to the intermediate transfer belt 12a as the irradiated member. The specular reflection light of light reflected by the intermediate transfer belt 12a (or toner adhering to the belt) when irradiation with the first irradiating light having passed through the light guiding path 60 is performed is guided to the light receiving element 34 through the light guiding path 61. Furthermore, the diffused reflection light of part of the light reflected by the intermediate transfer belt 12a (or toner adhering to the belt) when irradiation with the second irradiating light having passed through the light guiding path 63 is performed is guided to the light receiving element 35 through the light guiding path 62.

The light guiding path 61 is separated from the light guiding paths 60 and 62 by the light shielding wall 38. The light shielding wall 38 is provided so that the light receiving element 35 does not receive light (diffused reflection light from a light-receivable region 55 (to be described later) or the like) except for diffused reflection light from a light-receivable region 56 (to be described later). The light shielding wall 38 is formed integrally with the housing 37, provided above, in a vertical direction in relation to the mounting surface, the position of the light receiving element 35 on the mounting surface of the circuit board 36 (that is, immediately above the light receiving element 35), and formed up to near the opening of the housing 37. The light shielding wall 39 is provided between the LED 33 and the light receiving elements 34 and 35 in order to shield the light emitted from the LED 33 so that the light receiving elements 34 and 35 do not directly receive the light.

Note that as shown in FIG. 5A, in the housing 37 (a region between the LED 33 and the opening formed by the light shielding wall 38 and the inner wall of the housing), part of light guiding path 60 overlaps part of the light guiding path 62. This contributes to miniaturization of the toner detection unit 31.

(Irradiation Regions 54 and 58 of Light from LED 33)

The irradiation region 54, shown in FIG. 5A, of the light from the LED 33 corresponds to a region (first region) that is irradiated with the light (first irradiating light) from the LED 33 through the light guiding path 60 on the outer peripheral surface (the irradiated member) of the intermediate transfer belt 12a. The irradiation region 54 is defined by a light path connecting a left corner 60L of the light guiding path 60 and one edge of the LED 33 and a light path connecting a right corner 60R of the light guiding path 60 and the other edge of the LED 33.

The irradiation region 58 of the light from the LED 33 corresponds to a region (second region) that is irradiated with the light (second irradiating light) from the LED 33 through the light guiding path 63 on the outer peripheral surface (the irradiated member) of the intermediate transfer belt 12a. The irradiation region 58 is defined by a light path connecting a left corner 63L of the light guiding path 63 and one edge of the LED 33 and a light path connecting a right corner 63R of the light guiding path 63 and the other edge of the LED 33.

Note that as shown in FIG. 5A, when the light emitted from the LED 33 passes through the clear mold covering the LED 33 and the protection cover 49, the light is refracted in the clear mold and the protection cover 49. When the reflection light from the outer peripheral surface (irradiated member) of the intermediate transfer belt 12a passes through the protection cover 49 and the clear mold 48 covering the light receiving elements 34 and 35, the light is refracted.

(Light-Receivable Regions 55 and 56 of Light Receiving Elements 34 and 35)

The light-receivable region 55 of the light receiving element 34 shown in FIG. 5A corresponds to a region (range) on the outer peripheral surface (irradiated member) of the intermediate transfer belt 12a and a region where, if reflection light is generated by irradiating the region with the light, the light receiving element 34 can receive the reflection light. The light-receivable region 55 is defined by a straight line connecting a left corner 61L of the light guiding path 61 and one edge of the light receiving element 34 and a straight line connecting a right corner 61R of the light guiding path 61 and the other edge of the light receiving element 34. Note that in the example of FIGS. 5A and 5B, only a partial region 55' of the light-receivable region 55 is irradiated with the light (first irradiating light) from the LED 33, and thus the light receiving element 34 can receive reflection light from the region 55'. As described above, the light receiving element 34 according to the present embodiment is an example of the first light receiving element that receives specular reflection light specularly reflected by the irradiated member when irradiation with the first irradiating light is performed.

The light-receivable region 56 of the light receiving element 35 corresponds to a region (range) on the outer peripheral surface (irradiated member) of the intermediate transfer belt 12a and a region where, if reflection light is generated by irradiating the region with the light, the light receiving element 35 can receive the reflection light. The light-receivable region 56 is defined by a straight line connecting a left corner 62L of the light guiding path 62 and one edge of the light receiving element 35 and a straight line connecting a right corner 62R of the light guiding path 62 and the other edge of the light receiving element 35. Note that in the example of FIGS. 5A and 5B, only a partial region 56' of the light-receivable region 56 is irradiated with the light (second irradiating light) from the LED 33, and thus the light receiving element 35 can receive reflection light from the region 56'. As described above, the light receiving element 35 according to the present embodiment is an example of the second light receiving element that receives specular reflection light specularly reflected by the irradiated member when irradiation with the second irradiating light is performed.

(Light Path of Light Received by Each of Light Receiving Elements 34 and 35)

In the present embodiment, as shown in FIG. 5B, the light receiving element 34 is used to receive the light that is emitted from the LED 33, travels through the light guiding path 60 along an optical axis line 50, and is specularly reflected by the region 55' on the intermediate transfer belt 12a. Of the specular reflection light reflected by the region 55 (region 55'), specular reflection light that is reflected by a region 57 and travels along an optical axis line 51 reaches the light receiving element 34 and is received. Note that the light receiving element 34 also receives the diffused reflection light of the light with which a region except for the region 57 in the region 55' is irradiated.

The light receiving element 35 receives part of the light that is emitted from the LED 33, travels through the light guiding path 63 almost along an optical axis line 52, and is diffusely reflected by the region 56 (region 56') on the intermediate transfer belt 12a. Of the light diffusely reflected by the outer peripheral surface of the intermediate transfer belt 12a, diffused reflection light that travels through the light guiding path 62 almost along an optical axis line 53 reaches the light receiving element 35 and is received.

(Miniaturization of Toner Detection Unit 31)

Figure 6A:
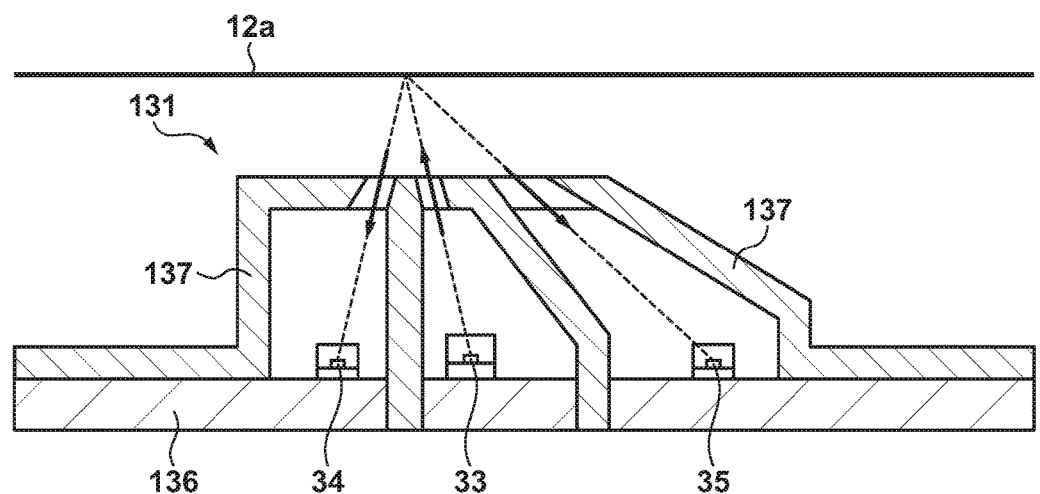
FIG. 6A and FIG. 6B are cross-sectional views illustrating a configuration of the toner detection unit which is a comparative example.

FIG. 6A is a cross-sectional view illustrating the configuration of a toner detection unit 131 according to a comparative example of the present embodiment. In the toner detection unit 131, two light receiving elements 34 and 35 that respectively receive the specular reflection light and diffused reflection light of light emitted from an LED 33 (light emitting element) are mounted as independent circuit elements on a circuit board 136. In accordance with this mounting, separate openings corresponding to the LED 33 and the two light receiving elements 34 and 35 are formed in a housing 137.

To the contrary, in the present embodiment, as shown in FIGS. 4, 5A, and 5B, the housing 37 is configured to mount the two light receiving elements 34 and 35 as one IC (in a state in which the two light receiving elements 34 and 35 are arranged side by side and packaged) on the circuit board 36. More specifically, the housing 37 of the toner detection unit 31 according to the present embodiment forms two openings opposing the protection cover 49 by the inner wall of the housing and the light shielding wall 38. That is, the housing 37 forms a common opening (first opening) through which the first irradiating light and the second irradiating light pass and the diffused reflection light to be received by the light receiving element 35 passes, and an opening (second opening) through which the specular reflection light to be received by the light receiving element 34 passes. With this configuration, the size of the toner detection unit 31 according to the present embodiment in a direction (a horizontal direction in FIG. 6A) in which the LED 33 and the two light receiving elements 34 and 35 are arranged can be miniaturized, as compared to the toner detection unit 131 according to the comparative example.

(Toner Detection Characteristic by Toner Detection Unit 31)

The toner detection unit 31 according to the present embodiment is configured so that the light receiving elements 34 and 35 respectively receive reflection light beams from the different light-receivable regions 55 and 56 (regions 55' and 56'). Therefore, the use of the toner detection unit 31 according to the present embodiment makes it possible to detect toner (toner images) in the two different regions (regions 55' and 56') on the intermediate transfer belt 12a at the same time. For example, the toner detection unit 31 is arranged so that the two light receiving elements 34 and 35 are arranged in a direction orthogonal to the movement direction of the surface of the intermediate transfer belt 12a. In this case, the regions 55' and 56' corresponding to the light receiving elements 34 and 35 are also arranged in the direction orthogonal to the movement direction of the surface of the intermediate transfer belt 12a. As a result, the use of the toner detection unit 31 makes it possible to detect toner images (for example, the test patterns 30) that respectively pass through the regions 55' and 56' at a timing when the rotational phases of the intermediate transfer belt 12a are the same.

The light receiving elements 34 and 35 of the toner detection unit 31 according to the present embodiment have different sensitivities to the density of the toner as a detection target due to the optical characteristic of the surface of the intermediate transfer belt 12a and the optical characteristic of the toner. More specifically, to improve the transferability of the toner image to the sheet, the surface of the intermediate transfer belt 12a generally has high smoothness and an optical characteristic of strong specular reflection. On the other hand, since the toner forming the toner image formed on the intermediate transfer belt 12a includes fine particles, scatter reflection in various directions is caused by irradiation with light. As the density of the toner to be irradiated with the light is higher, the light amount of the specular reflection light is smaller and the light amount of the diffused reflection light is larger.

Therefore, the light receiving element 34 has relatively high detection accuracy on the low density side, and the light receiving element 35 has relatively high detection accuracy on the high density side. The toner detection unit 31 according to the present embodiment can improve the toner detection accuracy using both the light receiving result of the specular reflection light by the light receiving element 34 and the light receiving result of the diffused reflection light by the light receiving element 35 by combining the light receiving elements 34 and 35.

As described above, the image forming apparatus 100 (control unit 41) according to the present embodiment can control an image forming condition based on a signal from the toner detection unit 31. For example, based on at least one of a signal output from the light receiving element 34 when the image (toner image) formed on the intermediate transfer belt 12a passes through the region 55' and a signal output from the light receiving element 35 when the image formed on the intermediate transfer belt 12a passes through the region 56', the control unit 41 may detect the position of the image and execute color misregistration correction control based on the detected position. Alternatively, based on at least one of the signal output from the light receiving element 34 when the image (toner image) formed on the intermediate transfer belt 12a passes through the region 55' and the signal output from the light receiving element 35 when the image formed on the intermediate transfer belt 12a passes through the region 56', the control unit 41 may detect the density of the image and execute image density control based on the detected density.

<Characteristics of Protection Cover 49 and Separation Component 59>

In the toner detection unit 31 according to the present embodiment, as shown in FIGS. 5A and 5B, the protection cover 49 mounted on the housing 37 covers the first opening on the side of the light guiding paths 60, 62, and 63 and the second opening on the side of the light guiding path 61, that are formed in an inlet portion to the housing 37. The protection cover 49 prevents, from entering the housing 37, dust such as paper dust generated in the image forming apparatus 100 and dust entering from the outside of the apparatus, thereby protecting the LED 33 and the two light receiving elements 34 and 35 from such dust.

In the toner detection unit 31 according to the present embodiment, the separation component 59 is provided between the LED 33 and the protection cover 49. The separation component 59 regulates the first irradiating light and the second irradiating light that have been separated by the separation component and the diffused reflection light to be received by the light receiving element 35 so as to be transmitted through different regions of the protection cover 49. In the example of FIG. 5A, the first irradiating light passing through the light guiding path 60 passes through a region 54c of the protection cover 49, and the second irradiating light passing through the light guiding path 63 is transmitted through a region 58c of the protection cover 49. The diffused reflection light to be received by the light receiving element 35 is transmitted through a region 56c of the protection cover 49. These regions 54c, 56c, and 58c are different (independent) regions. Note that in the toner detection unit 31 according to the present embodiment, the housing 37 (light shielding wall 38) is configured so that the reflection light to be received by the light receiving element 34 also passes through a region 55c of the protection cover 49, that is different from the regions 54c, 56c, and 58c.

As described above, the toner detection unit 31 is configured so that the regions 54c, 55c, 56c, and 58c of the protection cover 49 do not overlap each other while the irradiation regions 54 and 58 respectively overlap the light-receivable regions 55 and 56 on the intermediate transfer belt 12a. This can prevent deterioration of the toner detection accuracy even if dust contamination occurs when dust adheres to the protection cover 49. A mechanism capable of preventing, by the toner detection unit 31 of the present embodiment, deterioration of the toner detection accuracy caused by dust contamination occurring on the protection cover 49 will be described using a toner detection unit 231 shown in FIG. 6B as a comparative example.

Figure 6B:
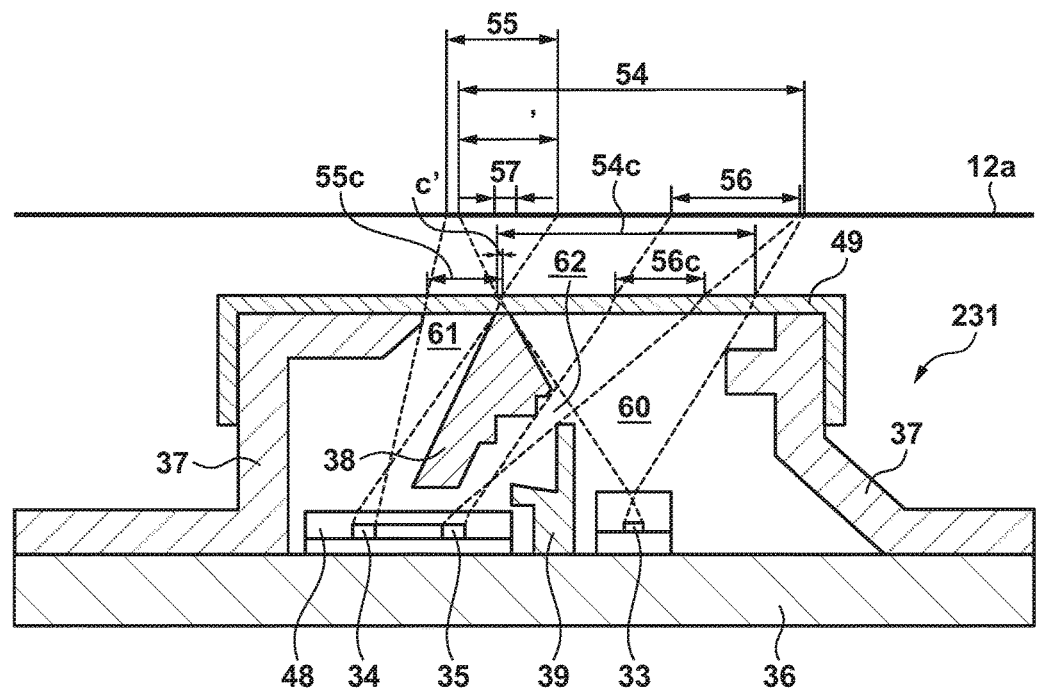

FIG. 6B is a cross-sectional view illustrating the configuration of the toner detection unit 231 according to the comparative example of the present embodiment. The toner detection unit 231 is different from the toner detection unit 31 (FIGS. 5A and 5B) according to the present embodiment in that no separation component 59 is provided. The toner detection unit 231 is also different from the toner detection unit 31 (FIGS. 5A and 5B) in terms of the shape of a portion of a light shielding wall 38, that contacts a protection cover 49. Since the toner detection unit 231 includes no separation component 59, irradiating light emitted from an LED 33 is not separated and the outer peripheral surface of an intermediate transfer belt 12a is irradiated with the irradiating light. In this case, an irradiation region 54 of the light from the LED 33 occupies a wide region that includes the irradiation regions 54 and 58 shown in FIGS. 5A and 5B and overlaps (at least partially) both the light-receivable regions 55 and 56.

In either of the toner detection units 31 and 231, if dust adheres to the protection cover 49, light transmitted through the protection cover 49 is blocked by the dust. As a result, the light amount of the irradiating light which is transmitted through the protection cover 49 and with which the intermediate transfer belt 12a (irradiated member) is irradiated decreases while the light amounts of the reflection light beams which are reflected by the intermediate transfer belt 12a and received by the light receiving elements 34 and 35 decrease. The decreases in received light amounts by the light receiving elements 34 and 35 can be compensated for by adjusting the light amount of the irradiating light emitted from the LED 33 and the amplification factors of the light receiving elements 34 and 35.

If the dust adhering to the protection cover 49 is irradiated with the light transmitted through the protection cover 49, diffused reflection occurs in a direction from the protection cover 49 toward the inside of the housing 37 since the dust includes fine particles. The diffused reflection light can be reflection light (to be referred to as "stray light" hereinafter) received by the light receiving element 34 or 35 without irradiating the intermediate transfer belt 12a. As will be described below, the toner detection unit 31 according to the present embodiment can reduce (or suppress) the influence of the stray light generated by the protection cover 49 on the received light amount by the light receiving element 34 or 35.

FIG. 7 is a view illustrating examples of the output characteristics of the light receiving elements 34 and 35 when toner images of different densities are sequentially formed on the intermediate transfer belt 12a, and the toner detection unit 231 according to the comparative example detects the formed toner images. FIG. 7 shows changes in outputs from the light receiving elements 34 and 35 when the test pattern 30 whose toner density gradually rises from 0% to 100% by 20% is formed on the intermediate transfer belt 12a and detected. Note that $V_1$ represents the output value (voltage) of the light receiving element 34, $V_2$ represents the output value (voltage) of the light receiving element 35, $V_{s1}$ represents a voltage (stray light level) corresponding to the received light amount of the stray light by the light receiving element 34, $V_{s2}$ represents a voltage (stray light level) corresponding to the received light amount of the stray light by the light receiving element 35, and $V_f$ represents an offset voltage of a circuit in the toner detection unit 31. Furthermore, FIG. 7 shows an output characteristic 701 before dust contamination occurs and an output characteristic 702 after dust contamination occurs. Note that the output characteristic 702 is a characteristic after adjusting the light amount of the irradiating light emitted from the LED 33 and the amplification factors of the light receiving elements 34 and 35.

In either of the output characteristics 701 and 702, the output value $V_1$ of the light receiving element 34 becomes a maximum value when reflection light from the surface of the intermediate transfer belt 12a on which no toner image is formed is received. This is caused by the optical characteristic of strong specular reflection of the intermediate transfer belt 12a. If reflection light from the test pattern 30 (toner image) is received, the output value $V_1$ of the light receiving element 34 becomes smaller as the density of the toner increases. This is because as the density of the toner increases, the light amount of the specular reflection light from the toner becomes smaller due to the diffused reflection characteristic of the toner.

The output value $V_2$ of the light receiving element 35 exhibits a change tendency opposite to that of the output value $V_1$ of the light receiving element 34 with respect to a change in density of the toner. More specifically, the output value $V_2$ of the light receiving element 35 becomes a minimum value when reflection light from the surface of the intermediate transfer belt 12a on which no test pattern 30 is formed is received. This is because the diffused reflection characteristic of the intermediate transfer belt 12a is weak. If the reflection light from the test pattern 30 (toner image) is received, the output value $V_2$ of the light receiving element 35 becomes larger as the density of the toner increases. This is because as the density of the toner increases, the light amount of the diffused reflection light from the toner becomes larger due to the diffused reflection characteristic of the toner.

By comparing the output characteristics 701 and 702 of FIG. 7 to each other, if dust contamination occurs, the stray levels $V_{s1}$ and $V_{s2}$ change to high level. This is because each of the light receiving elements 34 and 35 receives, as stray light, diffused reflection light generated when the dust adhering to the protection cover 49 is irradiated with the light from the LED 33.

More specifically, as shown in FIG. 6B, the light receiving element 34 receives stray light generated in a region 55c' overlapping the region 54c through which the irradiating light from the LED 33 passes within the region 55c, of the protection cover 49, through which the reflection light to be received by the light receiving element 34 passes. That is, the light receiving element 34 receives stray light generated by dust adhering to the boundary surface (surface) of the region 55c' on the side of the intermediate transfer belt 12a. Furthermore, the light receiving element 35 receives stray light generated in the region 56c through which the reflection light to be received by the light receiving element 35 passes and which is included in the region 54c, of the protection cover 49, through which the irradiating light from the LED 33 passes. That is, the light receiving element 35 receives stray light generated by dust adhering to the boundary surface (surface) of the region 55c on the side of the intermediate transfer belt 12a.

If the region through which the irradiating light from the LED 33 passes overlaps, in the protection cover 49, the regions (that is, the light-receivable regions) through which the reflection light beams to be received by the light receiving elements 34 and 35 pass, respectively, each of the light receiving element 34 and 35 receives stray light generated by the protection cover 49. As described above, if the light amount of the irradiating light emitted from the LED 33 and the amplification factors of the light receiving elements 34 and 35 are adjusted, the received light amount of the stray amount by each of the light receiving elements 34 and 35 increases as the dust adhering to the protection cover 49 increases. The increase in received light amount (stray level $V_{s1}$ or $V_{s2}$) of the stray light by each of the light receiving elements 34 and 35 degrades the toner detection accuracy of the toner detection unit 31.

In the output characteristic 702 shown in FIG. 7, the difference (an output value corresponding to a toner detection result) between the output value $V_1$ of the light receiving element 34 and the stray light level $V_{s1}$ is smaller than the stray light level $V_{s1}$ ($V_1-V_{s1}<V_{s1}$). Similarly, the difference (an output value corresponding to a toner detection result) between the output value $V_2$ of the light receiving element 35 and the stray light level $V_{s2}$ is smaller than the stray light level $V_{s2}$ ($V_2-V_{s2}<V_{s2}$). In this case, it becomes difficult to accurately detect toner based on the output value $V_1$ or $V_2$ due to the received light amount of the stray light.

Figure 8:
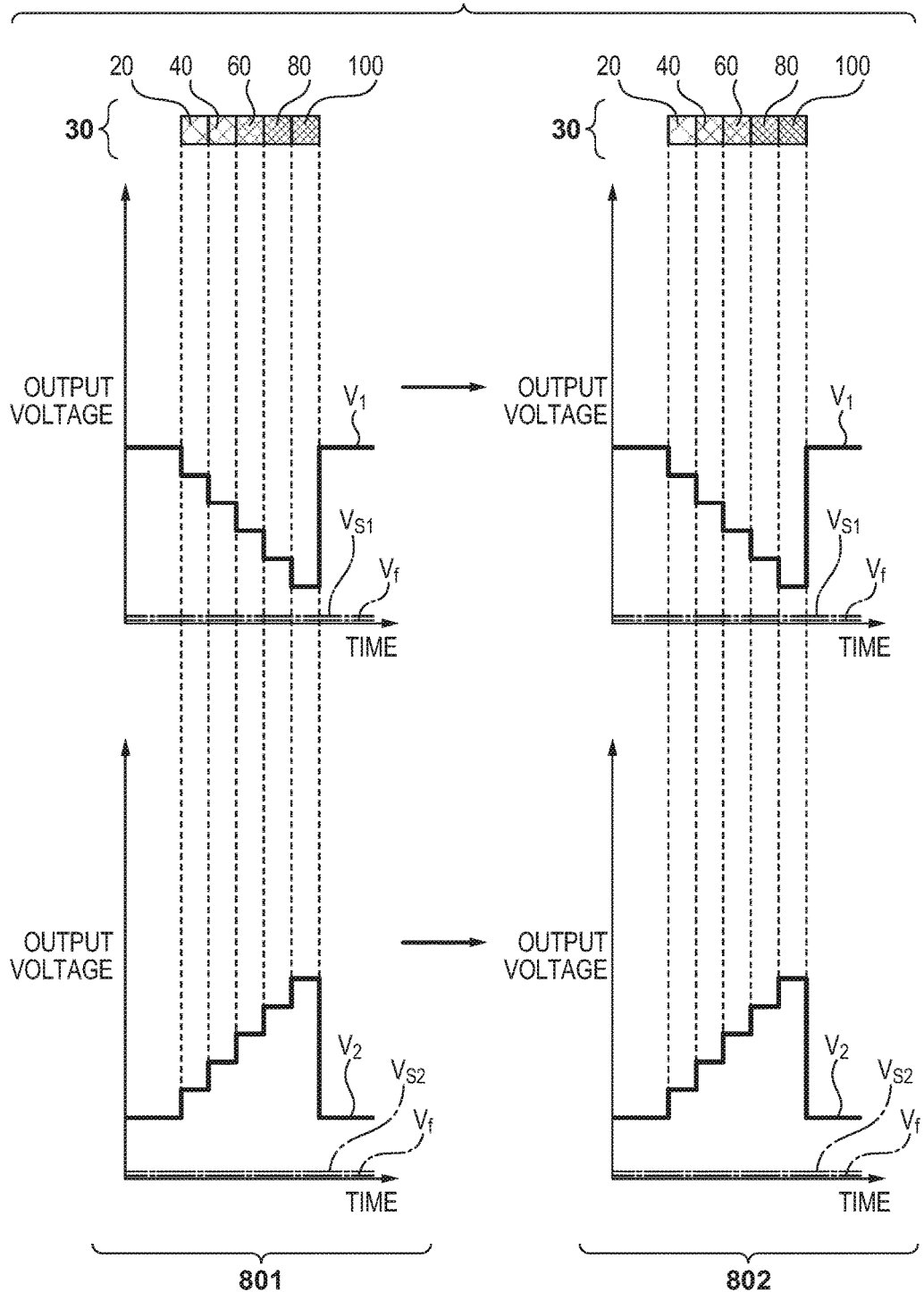
FIG. 8 illustrates examples of the output characteristics of light receiving elements 34 and 35 of the toner detection unit 31.

On the other hand, FIG. 8 is a view illustrating examples of the output characteristics of the light receiving elements 34 and 35 when toner images of different densities are sequentially formed on the intermediate transfer belt 12a, and the toner detection unit 31 according to the present embodiment detects the formed toner images. Note that FIG. 8 shows results of acquiring output characteristics 801 and 802 under the same condition as in FIG. 7.

In either of the output characteristics 801 and 802 shown in FIG. 8, even if dust contamination occurs, the stray light levels $V_{s1}$ and $V_{s2}$ remain the same, that is, the received light amount of the stray light by each of the light receiving elements 34 and 35 does not increase. Thus, the output values $V_1$ and $V_2$ of the light receiving elements 34 and 35 remain the same. This is because in the toner detection unit 31 according to the present embodiment, the region through which the irradiating light from the LED 33 passes does not overlap, in the protection cover 49, the regions (that is, the light-receivable regions) through which the reflection light beams to be received by the light receiving elements 34 and 35 pass respectively. That is, since the regions 55c and 56c are respectively different from the regions 54c and 58c, the light receiving elements 34 and 35 do not receive stray light beams generated in the regions 54c and 58c through which the first irradiating light and the second irradiating light from the LED 33 pass, respectively.

As described above, the toner detection unit 31 according to the present embodiment regulates, by the separation component 59, the first irradiating light, the second irradiating light, and the diffused reflection light to be received by the light receiving element 35 so as to be transmitted through different regions of the protection cover 49. This can prevent the stray light generated in the region of the protection cover 49, through which the irradiating light from the LED 33 passes, from being received by the light receiving element 35. Furthermore, in the toner detection unit 31 according to the present embodiment, the housing 37 (light shielding wall 38) is configured so that the first irradiating light passing through the light guiding path 60 and the reflection light to be received by the light receiving element 34 are transmitted through different regions of the protection cover 49. That is, the first and second openings formed in the housing 37 are used to regulate the first irradiating light and the reflection light reflected by the light-receivable region 55 (irradiated member) and received by the light receiving element 34 so as to be transmitted through different regions of the protection cover 49. This can prevent the stray light generated in the region of the protection cover 49, through which the irradiating light from the LED 33 passes, from being received by the light receiving element 34. Therefore, according to the present embodiment, it is possible to prevent the toner detection accuracy from deteriorating even if dust contamination occurs on the protection cover 49 while realizing miniaturization of the toner detection unit 31 (optical sensor).

<Other Characteristics of Toner Detection Unit 31>

Other characteristics of the toner detection unit 31 according to the present embodiment will be described next with reference to FIGS. 9 to 14. The toner detection unit 31 may have at least one of light shielding functions to be described below in order to further improve the toner detection accuracy.

(Shielding of Reflection Light from Separation Component 59)

Figure 9:
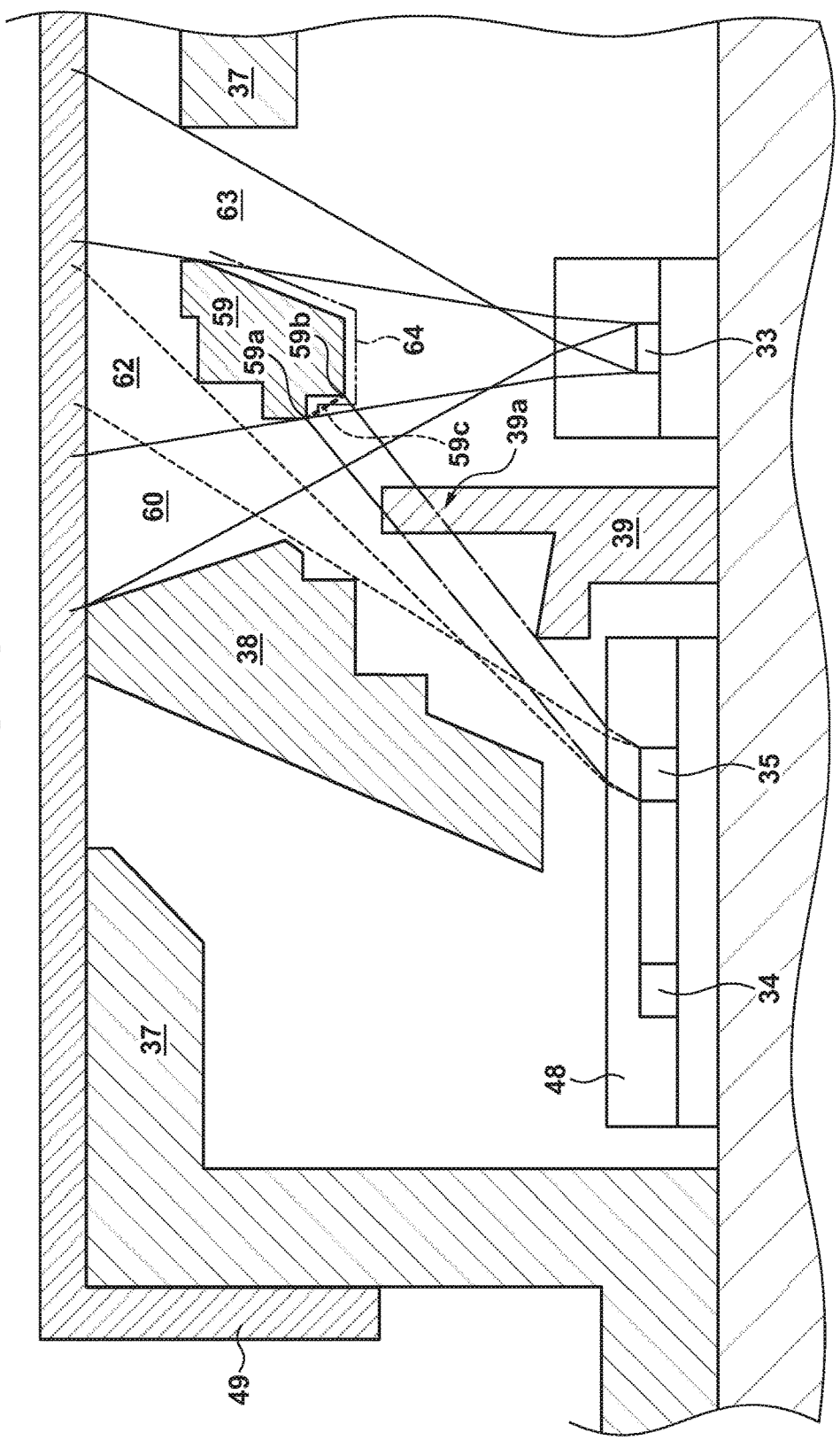
FIG. 9 is a cross-sectional view illustrating an example configuration of the toner detection unit 31.

FIG. 9 is a cross-sectional view illustrating an example of shielding of the reflection light generated by the separation component 59 when irradiation with the light from the LED 33 is performed. A surface 64, opposing the LED 33, of the separation component 59 is irradiated with the light from the LED 33. In this example, reflection light from the surface 64 of the separation component 59 is prevented from being received by each of the light receiving elements 34 and 35 as stray light. To implement this, as shown in FIG. 9, by including a projection 39a, the light shielding wall 39 can be formed to have a height that blocks the light emitted from the LED 33 and reflected by the surface of the separation component 59 toward the light receiving elements 34 and 35. The projection 39a can prevent the reflection light reflected by the surface 64 from being incident on the light receiving elements 34 and 35.

Referring to FIG. 9, a portion, on the side of the light receiving elements 34 and 35, of the surface 64 of the separation component 59 is formed by a horizontal surface 59a and a vertical surface 59b. In this example, even if an inclined surface 59c is provided in place of the horizontal surface 59a and the vertical surface 59b, the projection 39a can prevent reflection light reflected by the inclined surface 59c from being incident on the light receiving elements 34 and 35. Note that if the light shielding wall 39 has no sufficient height, formation of the surface 64 by the horizontal surface 59a and the vertical surface 59b is effective at reducing stray light traveling toward the light receiving elements 34 and 35.

As shown in FIG. 9, the surface of the projection 39a can be formed so as to prevent the light reflected by the separation component 59 from becoming reflection light (stray light) traveling toward the light receiving elements 34 and 35 even if the light is reflected by the projection 39a. The surface of the separation component 59 can be formed to have an angle that prevents the light emitted from the LED 33 from being reflected toward the light receiving elements 34 and 35.

(Shielding of Reflection Light from Boundary Surface of Protection Cover 49)

Figure 10:
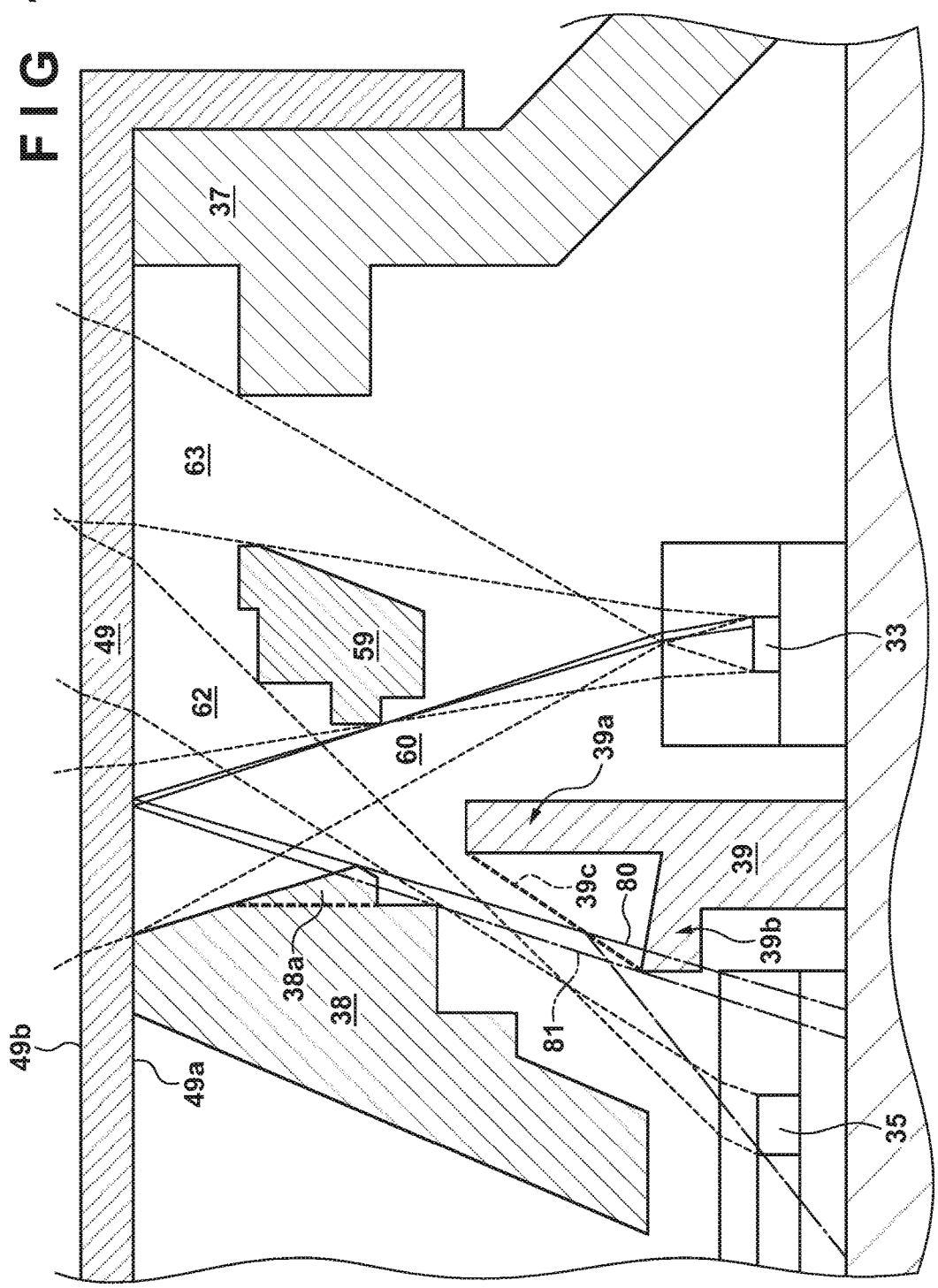
FIG. 10 is a cross-sectional view illustrating the example configuration of the toner detection unit 31.
Figure 11:
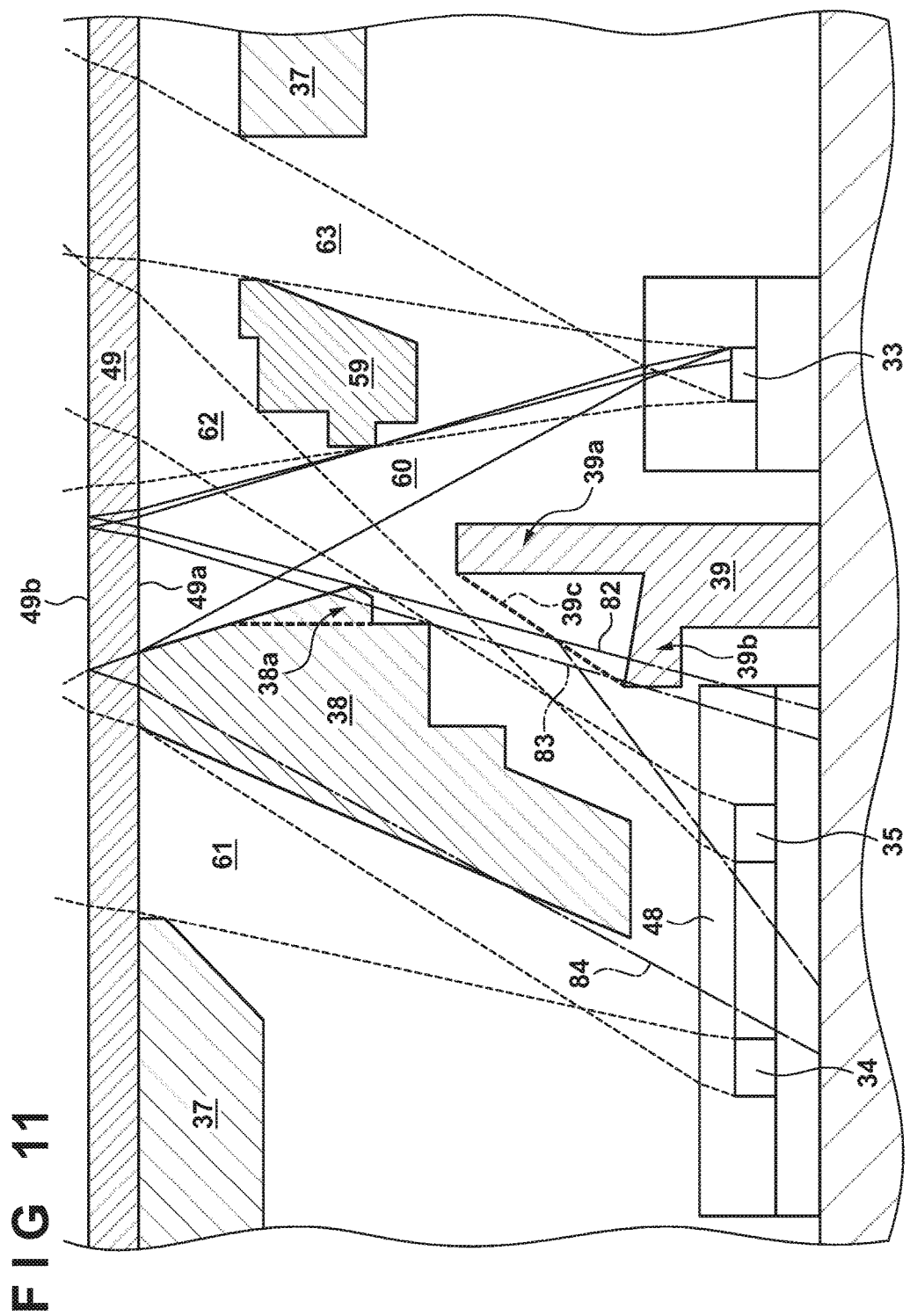
FIG. 11 is a cross-sectional view illustrating the example configuration of the toner detection unit 31.
Figure 12:
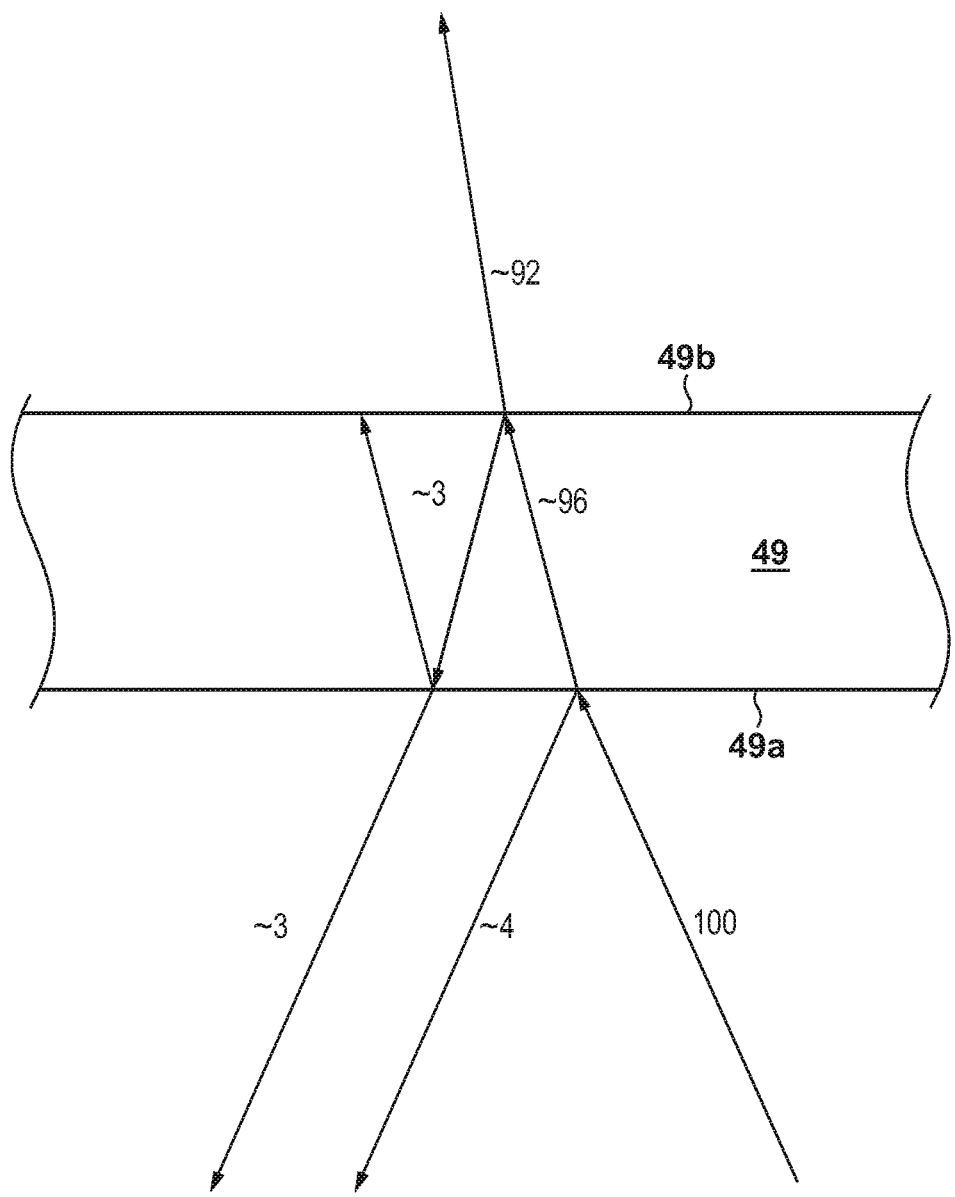
FIG. 12 illustrates an example of reflection and refraction of light occurring on boundary surfaces 49a and 49b of a protection cover 49.

FIG. 10 is a cross-sectional view illustrating an example of shielding of reflection light generated by a boundary surface 49a, opposing the housing 37, of the protection cover 49. FIG. 11 is a cross-sectional view illustrating an example of shielding of reflection light generated by a boundary surface 49b, opposing the housing 37, of the protection cover 49. Note that the protection cover 49 includes the boundary surface 49a and the boundary surface 49b on the opposite side of the boundary surface 49a. The protection cover 49 is made of a material having a transmissive property, such as glass or acrylic, and has an inherent refractive index in accordance with the material. The boundary surfaces 49a and 49b correspond to a portion where a difference is generated between the atmospheric refractive index and the refractive index of the protection cover 49. Therefore, as shown in FIG. 12, the irradiating light from the LED 33 is partially transmitted through the boundary surface 49a or 49b, and partially reflected by the boundary surface 49a or 49b.

In the example of FIG. 10, reflection light from the boundary surface 49a of the protection cover 49 is prevented from being received by the light receiving elements 34 and 35 as stray light. To implement this, the light shielding wall 38 can be formed to have a projection 38a that projects toward the LED 33 and is formed to block light beams 80 and 81 emitted from the LED 33 and reflected by the boundary surface 49a toward the light receiving elements 34 and 35. The projection 38a can prevent the reflection light reflected by the boundary surface 49a from being incident on the light receiving elements 34 and 35.

In the example of FIG. 11, the reflection light from the boundary surface 49a of the protection cover 49 is prevented from being received by the light receiving elements 34 and 35 as stray light. To implement this, as shown in FIG. 11, the projection 38a of the light shielding wall 38 can be formed to block light beams 82 and 83 emitted from the LED 33, transmitted through the boundary surface 49a, and reflected by the boundary surface 49b toward the light receiving element 35.

Note that even if the reflection light beams 80 to 83 are not directly incident on the light receiving elements 34 and 35, they may be incident on the clear mold 48 to repeat internal reflection in the clear mold 48, and then received by the light receiving elements 34 and 35. To cope with this, as shown in FIGS. 10 and 11, it is effective to provide the projection 38a on the upstream side as much as possible in the traveling direction of the reflection light beams in terms of prevention of the reflection light beams 80 to 83 from being incident on the clear mold 48.

In the example shown in FIGS. 10 and 11, the light shielding wall 39 can be formed to have a projection 39b projecting toward the light receiving elements 34 and 35.

The projection 39*b* is provided to block the light beams 80 to 82 emitted from the LED 33 and reflected by the boundary surfaces 49*a* and 49*b* toward the light receiving elements 34 and 35. This can prevent the reflection light beams 80 to 83 generated by the boundary surfaces 49*a* and 49*b* from being incident on the light receiving elements 34 and 35 by blocking them by the projection 39*b* even if the projection 39*b* cannot be shielded from the light beams.

The surface of the projection 39*b* can be formed to have an angle that prevents the light beams 80 to 82 emitted from the LED 33 and reflected by the boundary surfaces 49*a* and 49*b* from being reflected toward the light receiving elements 34 and 35. This can decrease the possibility that the reflection light beams 80 to 82 become stray light beams received by the light receiving elements 34 and 35.

In the example of FIG. 11, furthermore, the light shielding wall 38 can be formed to block light 84 emitted from the LED 33, transmitted through the boundary surface 49*a*, and reflected by the boundary surface 49*b* toward the light receiving element 34. More specifically, the light shielding wall 38 can be formed to contact the boundary surface 49*a* of the protection cover 49. This can prevent the reflection light 84 generated by the boundary surface 49*b* from being incident on the light receiving element 34.

Note that in this example, each of the boundary surfaces 49*a* and 49*b* is formed to be parallel to the outer peripheral surface of the intermediate transfer belt 12*a*, but the angles of the boundary surfaces 49*a* and 49*b* may be set so that the reflection light beams generated by the boundary surfaces 49*a* and 49*b* do not travel toward the light receiving elements 34 and 35.

(Shielding of Reflection Light from Irradiation Region 54 or 58)

Figure 13:
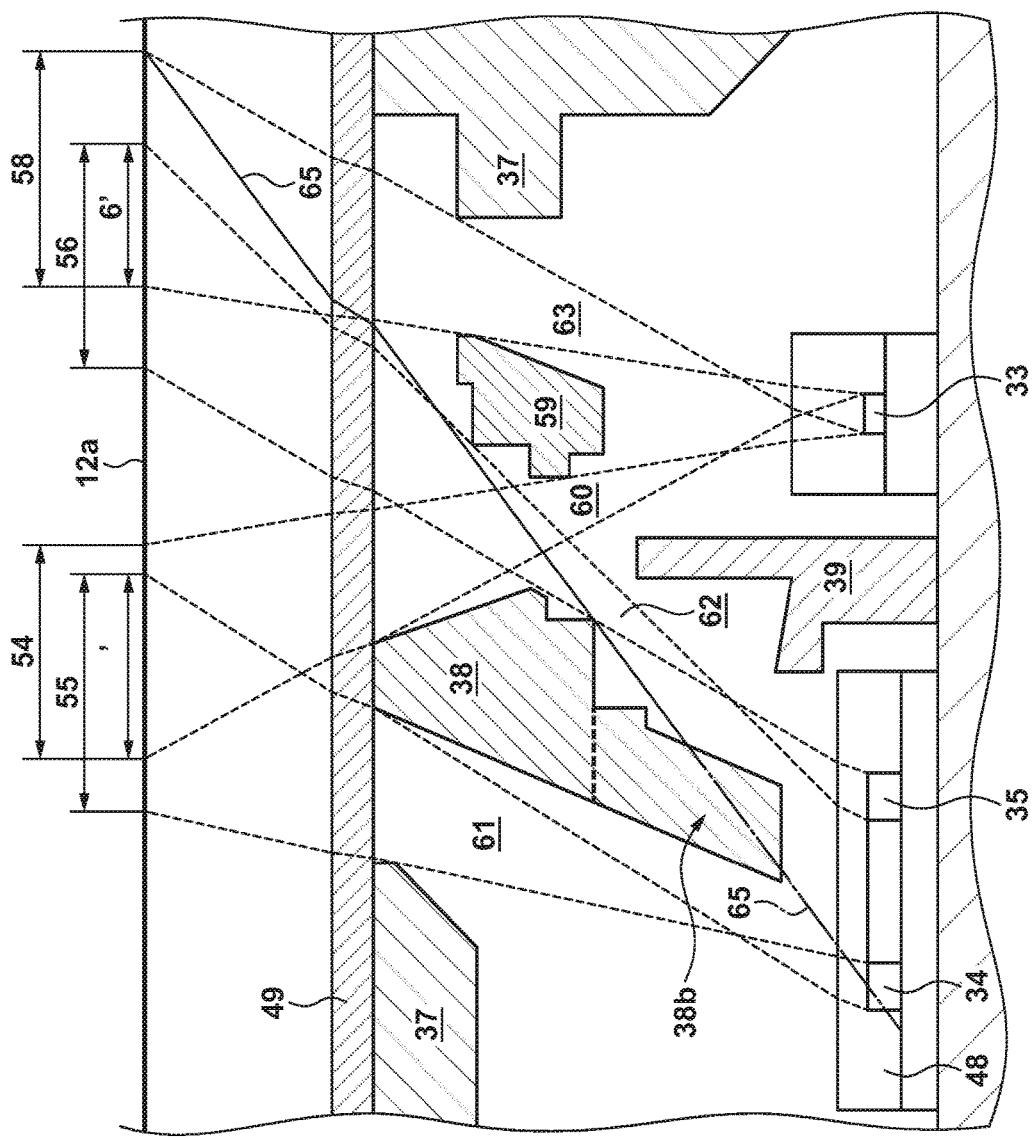
FIG. 13 is a cross-sectional view illustrating an example configuration of the toner detection unit 31.

FIG. 13 is a cross-sectional view illustrating an example of shielding of reflection light from the irradiation region 58 on the intermediate transfer belt 12*a*. The toner detection unit 31 needs to prevent the reflection light from the irradiation region 58 from being received by the light receiving element 34 for receiving the specular reflection light from the light-receivable region 55 (region 55'). To implement this, by including a projection 38*b*, the light shielding wall 38 can be formed to block the light 65 diffusely reflected by the irradiation region 58 toward the light receiving element 34.

Figure 14:
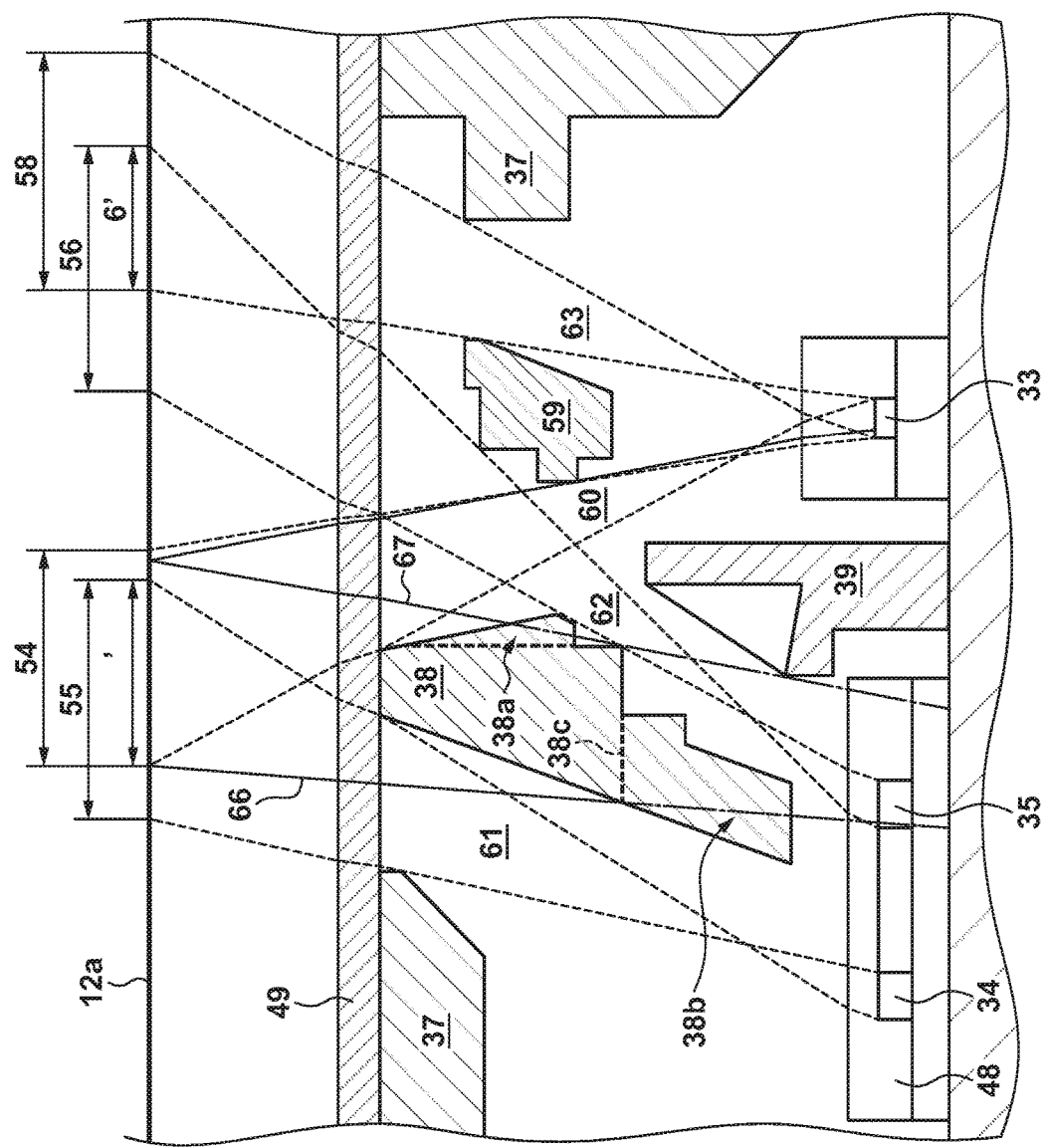
FIG. 14 is a cross-sectional view illustrating an example configuration of the toner detection unit 31.

FIG. 14 is a cross-sectional view illustrating an example of shielding of the reflection light from the irradiation region 54 on the intermediate transfer belt 12*a*. The toner detection unit 31 needs to prevent the reflection light from the irradiation region 54 from being received by the light receiving element 35 for receiving the diffused reflection light from the light-receivable region 56 (region 56'). To implement this, the projection 38*a* of the light shielding wall 38 can be formed to block the light 67 diffusely reflected by the irradiation region 54 toward the light receiving element 35.

In the example of FIG. 14, furthermore, the projection 38*b* can be formed to block light 66 diffusely reflected by the irradiation region 54 toward the light receiving element 35. If there is no projection 38*b* in the lower portion of the light shielding wall 38 and the lower surface of the light shielding wall 38 is formed by a horizontal surface 38*c*, the reflection light 66 from the irradiation region 54 is incident on the light receiving element 35. However, by providing the projection 38*b* shown in FIG. 14 in the light shielding wall 38, the reflection light 66 can be prevented from being incident on the light receiving element 35.

As described above, in the toner detection unit 31 according to the present embodiment, the LED 33 emits the irradiating light with which the irradiated member (intermediate transfer belt 12*a*) is irradiated. The separation component 59 separates the irradiating light emitted from the LED 33 into the first irradiating light and the second irradiating light. The light receiving element 34 receives the specular reflection light specularly reflected by the irradiated member when irradiation with the first irradiating light is performed. The light receiving element 35 receives the diffused reflection light diffusely reflected by the irradiated member when irradiation with the second irradiating light is performed. The housing 37 forms the first opening through which the first irradiating light and the second irradiating light pass and the diffused reflection light to be received by the light receiving element 35 passes, and the second opening through which the specular reflection light to be received by the light receiving element 34 passes. The protection cover 49 has a light transmissive property and covers the first and second openings. The separation component 59 is provided at a position between the LED 33 and the protection cover 49, and regulates the first irradiating light, the second irradiating light, and the diffused reflection light to be received by the light receiving element 35 so as to be transmitted through different regions of the protection cover 49. According to the present embodiment, it is possible to prevent the toner detection accuracy from deteriorating even if dust contamination occurs on the protection cover 49 while realizing miniaturization of the toner detection unit 31.

Second Embodiment

The second embodiment will describe an example in which in order to increase the received light amount of a light receiving element 35, a condensing component that condenses at least one of the first irradiating light and diffused reflection light to be received by the light receiving element 35 is provided in the protection cover 49 according to the first embodiment. Note that the difference from the first embodiment will be described below.

Figure 15:
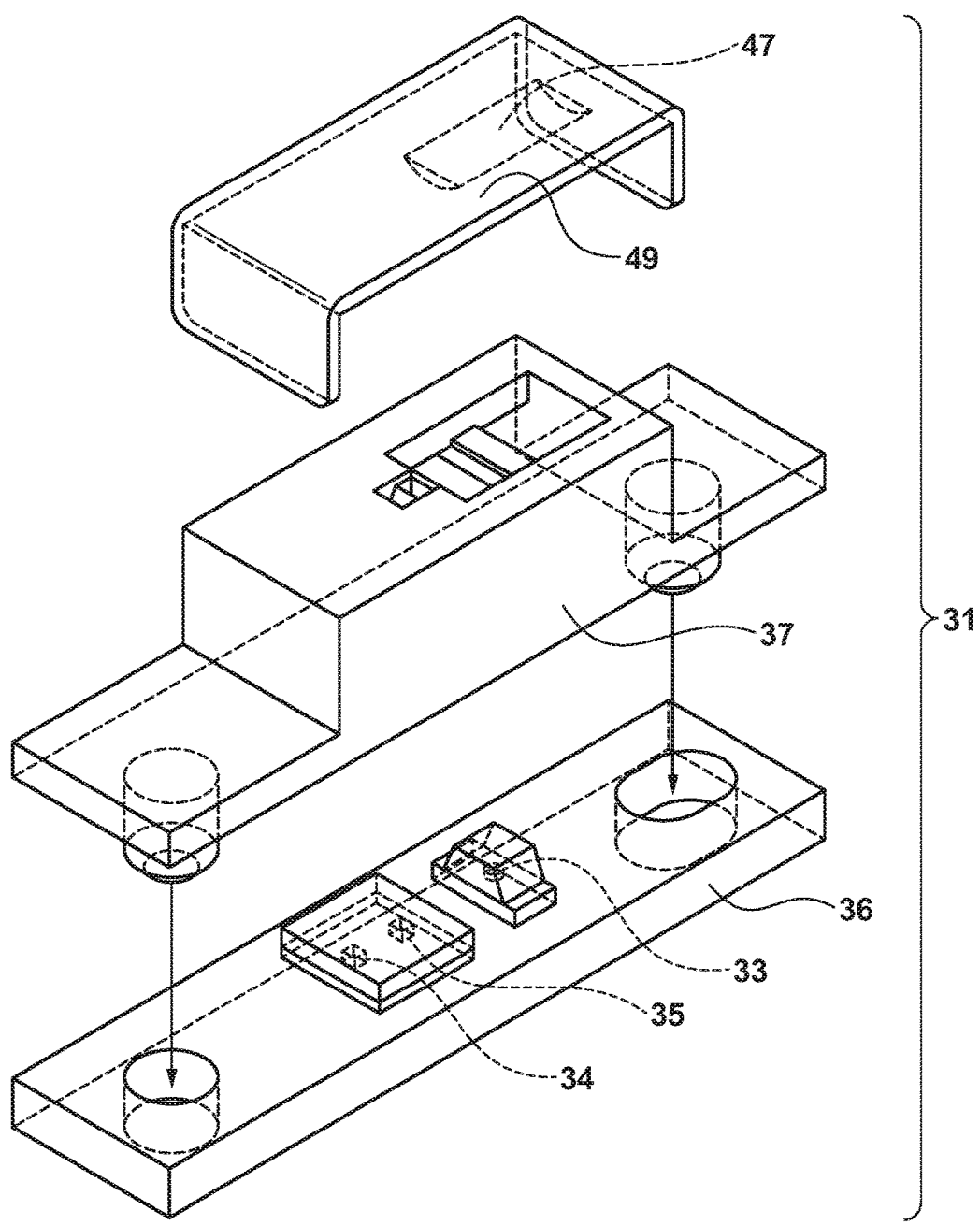
FIG. 15 is a perspective view illustrating an example configuration of a toner detection unit (second embodiment).
Figure 16:
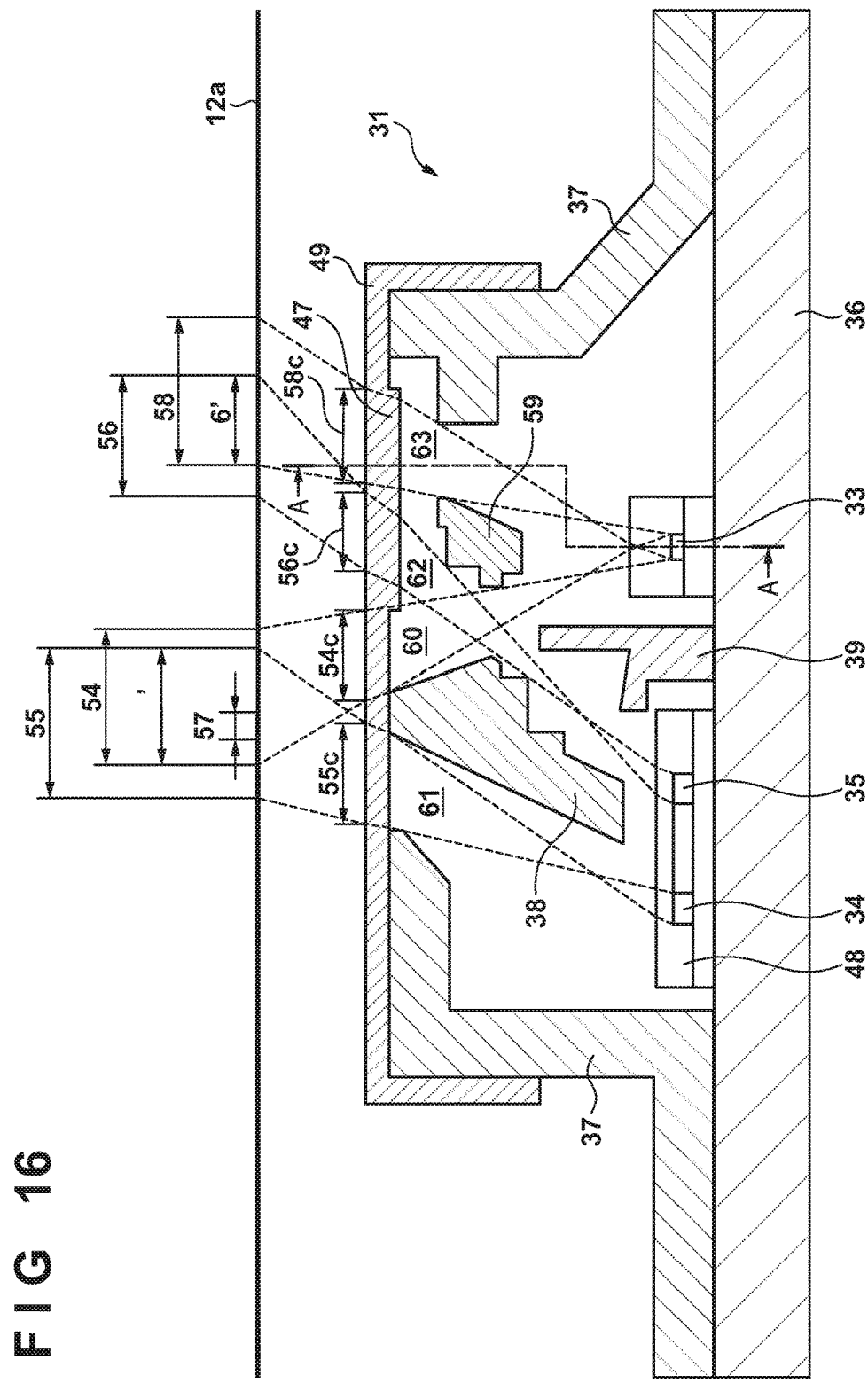
FIG. 16 is a cross-sectional view illustrating the example configuration of the toner detection unit (second embodiment).
Figure 17:
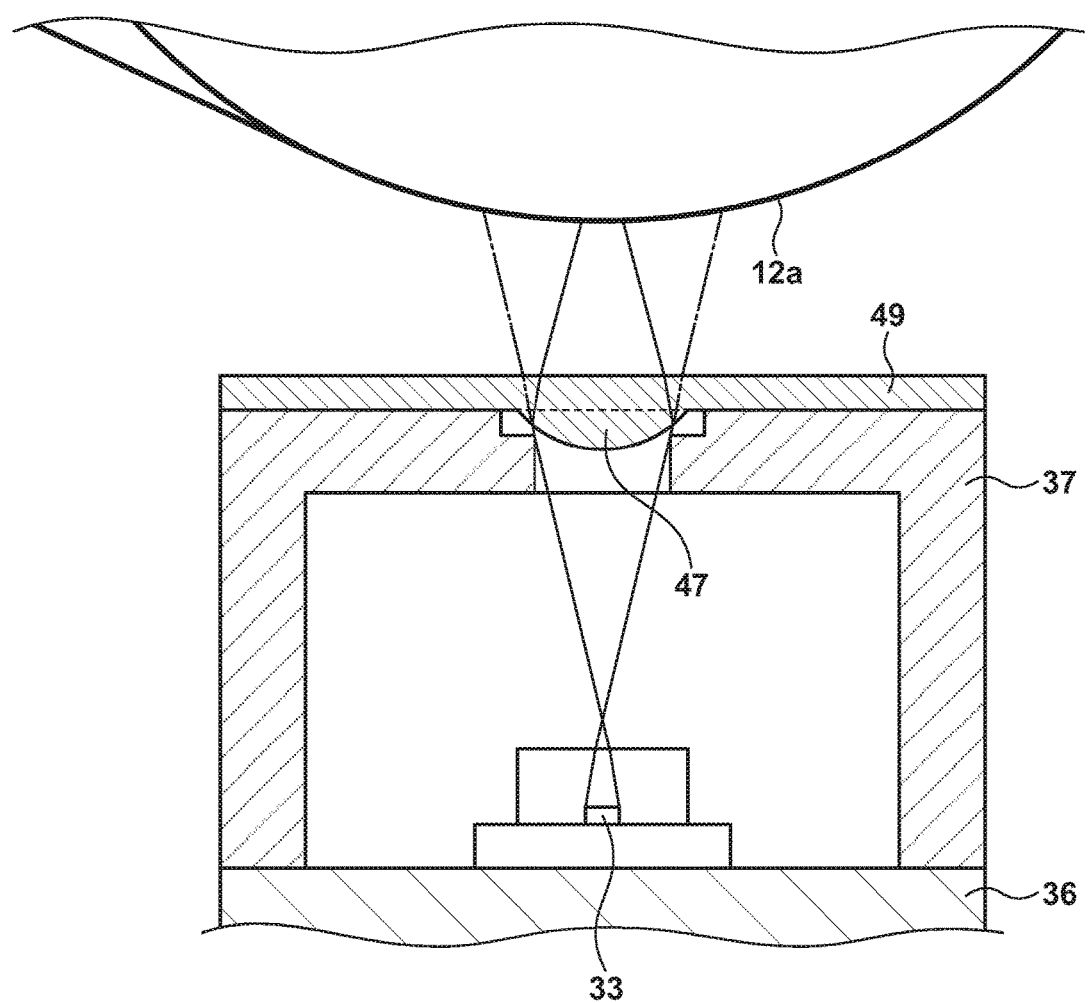
FIG. 17 is a cross-sectional view illustrating an example configuration of a condensing component 47 (second embodiment).

FIGS. 15 and 16 are a perspective view and a schematic cross-sectional view each showing an example configuration of a toner detection unit 31 according to the second embodiment. FIG. 17 is a cross-sectional view taken along a line A-A of a light guiding path 63 in FIG. 16. As shown in FIG. 15, the toner detection unit 31 according to the present embodiment is different from that according to the first embodiment in that a condensing component 47 is provided in the protection cover 49.

A light-receivable region 56 of the toner detection unit 31 is narrower than the light-receivable region 56 (FIG. 6B) of the toner detection unit 231 according to the comparative example. This is because the irradiation region of irradiating light from an LED 33 and a light-receivable region corresponding to the light receiving element 35 are restricted by a separation component 59. This decreases the received light amount of the light receiving element 35.

In this embodiment, the condensing component 47 is provided in the protection cover 49 to compensate for the decrease in received light amount of the light receiving element 35, that is caused by the restriction of the light-receivable region 56. As shown in FIG. 17, the condensing component 47 condenses, in the movement direction (sub scanning direction) of the surface of an intermediate transfer belt 12*a*, the second irradiating light traveling from the LED 33 to an irradiation region 58, and also condenses, in the sub scanning direction, the diffused reflection light traveling from a region 56' to the light receiving element 35. This can increase the received light amount of the light receiving element 35. Note that FIGS. 15 and 17 show the condensing component 47 having a cylindrical shape. However, the condensing component 47 may have a spherical shape, an elliptic shape, or a Fresnel lens shape.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-077734, filed Apr. 10, 2017, which is hereby incorporated by reference herein in its entirety.

What is claimed is:

1. An optical sensor comprising:
a light emitting element configured to emit irradiating light with which an irradiated member is irradiated;
a separation component configured to separate the irradiating light into first irradiating light and second irradiating light;
a first light receiving element configured to receive specular reflection light specularly reflected by the irradiated member when irradiation with the first irradiating light is performed;
a second light receiving element configured to receive diffused reflection light diffusely reflected by the irradiated member when irradiation with the second irradiating light is performed; and
a housing configured to form a first opening through which the first irradiating light and the second irradiating light pass and the diffused reflection light to be received by the second light receiving element passes, and a second opening through which the specular reflection light to be received by the first light receiving element passes,
wherein when a first region on the irradiated member is irradiated with the first irradiating light, and a second region different from the first region on the irradiated member is irradiated with the second irradiating light, the first light receiving element receives the specular reflection light specularly reflected by the first region, and the second light receiving element receives the diffused reflection light diffusely reflected by the second region.

2. The sensor according to claim 1, further comprising a cover component having a light transmissive property and configured to cover the first opening and the second opening, wherein the separation component is provided at a position between the light emitting element and the cover component, and regulates the first irradiating light, the second irradiating light, and the diffused reflection light to be received by the second light receiving element so as to be transmitted through different regions of the cover component.

3. The sensor according to claim 2, wherein the first opening and the second opening regulate the first irradiating light and reflection light reflected by the irradiated member and received by the first light receiving element so as to be transmitted through different regions of the cover component.

4. The sensor according to claim 2, wherein the housing has a light shielding wall provided above, in a vertical direction in relation to a mounting surface of a circuit board on which the first light receiving element and the second light receiving element are mounted, a position of the first light receiving element on the mounting surface, and configured to shield light except for the diffused reflection light so as not to be received by the second light receiving element.

5. The sensor according to claim 4, wherein the cover component has a first boundary surface opposing the housing and a second boundary surface on an opposite side of the first boundary surface, and the light shielding wall has a projection that projects toward the light emitting element and is formed to block light emitted from the light emitting element and reflected by the first boundary surface toward the first light receiving element and the second light receiving element.

6. The sensor according to claim 5, wherein the projection is formed to further block light emitted from the light emitting element, transmitted through the first boundary surface, and reflected by the second boundary surface toward the second light receiving element, and is formed to further block light diffusely reflected, toward the second light receiving element, by the first region irradiated with the first irradiating light on the irradiated member.

7. The sensor according to claim 4, wherein the cover component has a first boundary surface opposing the housing and a second boundary surface on an opposite side of the first boundary surface, and the light shielding wall is formed to block light emitted from the light emitting element, transmitted through the first boundary surface, and reflected by the second boundary surface toward the first light receiving element.

8. The sensor according to claim 4, wherein the light shielding wall is formed to block light diffusely reflected, toward the first light receiving element, by the second region irradiated with the second irradiating light on the irradiated member, or the light shielding wall is formed to block light diffusely reflected, toward the second light receiving element, by the first region irradiated with the first irradiating light on the irradiated member.

9. The sensor according to claim 2, wherein the housing has a light shielding wall provided between the light emitting element and the second light receiving element, and configured to shield the light emitted from the light emitting element so as not to be directly received by the first light receiving element and the second light receiving element, and the light shielding wall is formed to have a height that blocks the light emitted from the light emitting element and reflected by a surface of the separation component toward the first light receiving element and the second light receiving element.

10. The sensor according to claim 9, wherein the cover component includes a first boundary surface opposing the housing and a second boundary surface on an opposite side of the first boundary surface, the light shielding wall includes a projection that projects toward the first light receiving element and the second light receiving element and is formed to block the light emitted from the light emitting element and reflected by the first boundary surface toward the first light receiving element and the second light receiving element, and a surface of the projection of the light shielding wall is formed to have an angle that prevents the light emitted from the light emitting element and reflected by the first boundary surface from being reflected toward the first light receiving element and the second light receiving element.

11. The sensor according to claim 2, wherein the cover component includes a condensing component configured to condense at least one of the first irradiating light and the diffused reflection light that are transmitted through the cover component, and the condensing component has one of a cylindrical shape, a spherical shape, an elliptic shape, and a Fresnel lens shape.

12. The sensor according to claim 1, wherein in a region between the light emitting element and the first opening, part of a light path through which the first irradiating light passes overlaps part of a light path through which the diffused reflection light to be received by the second light receiving element passes.

13. The sensor according to claim 1, wherein the housing forms, in a region between the second light receiving element and the first opening, a third opening that regulates the diffused reflection light having passed through the first opening and through which the diffused reflection light to be received by the second light receiving element passes.

14. The sensor according to claim 1, wherein a surface of the separation component is formed to have an angle that prevents the light emitted from the light emitting element from being reflected toward the first light receiving element and the second light receiving element.

15. The sensor according to claim 1, wherein the housing includes:
a first light shielding wall provided above, in a vertical direction in relation to a mounting surface of a circuit board on which the first light receiving element and the second light receiving element are mounted, a position of the first light receiving element on the mounting surface, and configured to shield light except for the diffused reflection light so as not to be received by the second light receiving element, and
a second light shielding wall provided between the light emitting element and the second light receiving element, and configured to shield the light emitted from the light emitting element so as not to be directly received by the first light receiving element and the second light receiving element,
wherein the first light shielding wall and the second light shielding wall form, in a region between the first opening and the second light receiving element, a third opening that regulates the diffused reflection light having passed through the first opening and through which the diffused reflection light to be received by the second light receiving element passes.

16. The sensor according to claim 1, wherein the light emitting element, the first light receiving element, and the second light receiving element are arranged in a line, and a linear distance between the second light receiving element and the light emitting element is shorter than a linear distance between the first light receiving element and the light emitting element.

17. The sensor according to claim 1, wherein the first light receiving element and the second light receiving element are arranged to be adjacent to each other on a circuit board.

18. The sensor according to claim 1, wherein the separation component is formed integrally with the housing.

19. The sensor according to claim 1, wherein the first light receiving element and the second light receiving element are mounted as one integrated circuit on a circuit board.

20. An image forming apparatus comprising:
an image carrier;
an image forming unit configured to form an image on the image carrier;
an optical sensor provided at a position opposing a surface of the image carrier and configured to irradiate the image carrier as an irradiated member with light from a light emitting element; and
a control unit configured to control an image forming condition of the image forming unit based on a signal from the optical sensor,
wherein the optical sensor comprises:
the light emitting element configured to emit irradiating light with which the irradiated member is irradiated;
a separation component configured to separate the irradiating light into first irradiating light and second irradiating light;
a first light receiving element configured to receive specular reflection light specularly reflected by the irradiated member when irradiation with the first irradiating light is performed;
a second light receiving element configured to receive diffused reflection light diffusely reflected by the irradiated member when irradiation with the second irradiating light is performed; and
a housing configured to form a first opening through which the first irradiating light and the second irradiating light pass and the diffused reflection light to be received by the second light receiving element passes, and a second opening through which the specular reflection light to be received by the first light receiving element passes,
wherein when a first region on the irradiated member is irradiated with the first irradiating light, and a second region different from the first region on the irradiated member is irradiated with the second irradiating light, the first light receiving element receives the specular reflection light specularly reflected by the first region, and the second light receiving element receives the diffused reflection light diffusely reflected by the second region.

21. The apparatus according to claim 20, wherein based on at least one of a signal output from the first light receiving element when the image formed on the image carrier passes through the first region irradiated with the first irradiating light and a signal output from the second light receiving element when the image formed on the image carrier passes through the second region irradiated with the second irradiating light, the control unit detects a position of the image and executes color misregistration correction control based on the detected position of the image.

22. The apparatus according to claim 20, wherein based on at least one of the signal output from the first light receiving element when the image formed on the image carrier passes through the first region irradiated with the first irradiating light and the signal output from the second light receiving element when the image formed on the image carrier passes through the second region irradiated with the second irradiating light, the control unit detects a density of the image and executes image density control based on the detected density of the image.

* * * * *